United States Patent
Zhu et al.

(10) Patent No.: US 12,103,941 B2
(45) Date of Patent: Oct. 1, 2024

(54) RADIATION-ACTIVATABLE PLATINUM COMPLEX, ITS PREPARATION AND THERAPEUTIC USE

(71) Applicant: City University of Hong Kong, Kowloon (HK)

(72) Inventors: Guangyu Zhu, Pok Fu Lam (HK); Gongyuan Liu, Lanzhou (CN)

(73) Assignee: City University of Hong Kong, Kowloon (HK)

(*) Notice: Subject to any disclaimer, the term of this patent is extended or adjusted under 35 U.S.C. 154(b) by 0 days.

(21) Appl. No.: 18/045,210

(22) Filed: Oct. 10, 2022

(65) Prior Publication Data

US 2024/0132529 A1    Apr. 25, 2024

(51) Int. Cl.
*C07F 15/00* (2006.01)
*A61K 41/00* (2020.01)
*A61P 35/00* (2006.01)

(52) U.S. Cl.
CPC ...... *C07F 15/0013* (2013.01); *A61K 41/0033* (2013.01); *A61K 41/0057* (2013.01); *A61P 35/00* (2018.01)

(58) Field of Classification Search
CPC .. C07F 15/0013; A61P 35/00; A61K 41/0033; A61K 41/0057
USPC ........................................................ 514/186
See application file for complete search history.

(56) References Cited

FOREIGN PATENT DOCUMENTS

WO    WO 2016106324    *    6/2016    ............. A61K 47/48

OTHER PUBLICATIONS

Lai Y, Lu N, Ouyang A, Zhang Q, Zhang P. Ferroptosis promotes sonodynamic therapy: a platinum (II)-indocyanine sonosensitizer. Chemical Science. 2022;13(34):9921-6. (Year: 2022).*
Yao H, Gunawan YF, Liu G, Tse MK, Zhu G. Optimization of axial ligands to promote the photoactivation of BODIPY-conjugated platinum (IV) anticancer prodrugs. Dalton Transactions. 2021;50(39):13737-47. (Year: 2021).*
Yao H, Gunawan YF, Liu G, Tse MK, Zhu G. Optimization of axial ligands to promote the photoactivation of BODIPY-conjugated platinum (IV) anticancer prodrugs. Dalton Transactions. 2021;50(39): Supplementary Information, 97 pages. (Year: 2021).*
Yamane T, Hanaoka K, Muramatsu Y, Tamura K, Adachi Y, Miyashita Y, Hirata Y, Nagano T. Method for enhancing cell penetration of Gd3+-based MRI contrast agents by conjugation with hydrophobic fluorescent dyes. Bioconjugate chemistry. Nov. 16, 2011;22(11):2227-36. (Year: 2011) (Year: 2011).*

* cited by examiner

*Primary Examiner* — Jeffrey S Lundgren
*Assistant Examiner* — Heather Dahlin
(74) *Attorney, Agent, or Firm* — Renner, Kenner, Greive, Bobak, Taylor & Weber

(57) ABSTRACT

A platinum complex having a structure of Formula (I) particularly of Formula (A) such as Formula (III) or Formula (IIIa). A pharmaceutical composition includes the platinum complex of the present invention and a pharmaceutically acceptable carrier. A method of treating a target tissue includes administering to a patient in need thereof a platinum complex of the present invention and administering to the target tissue radiation in an amount and of a frequency effective to activate the compound. The platinum complex of the present invention can be used in preparation of a medicament for treating the target tissue by sonodynamic therapy, photodynamic therapy, chemotherapy and/or a combination thereof.

19 Claims, 19 Drawing Sheets

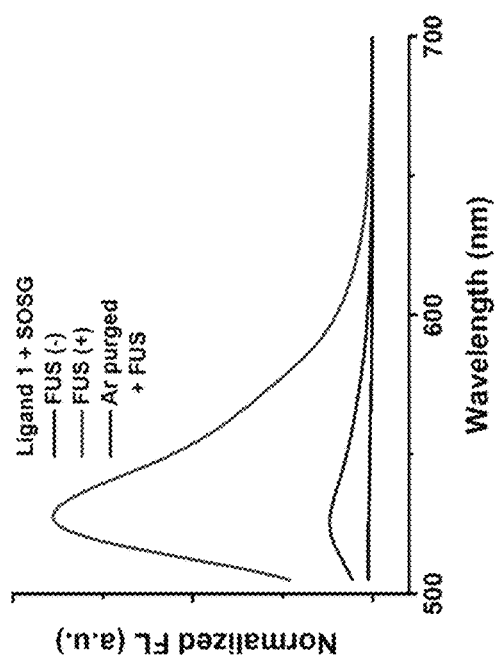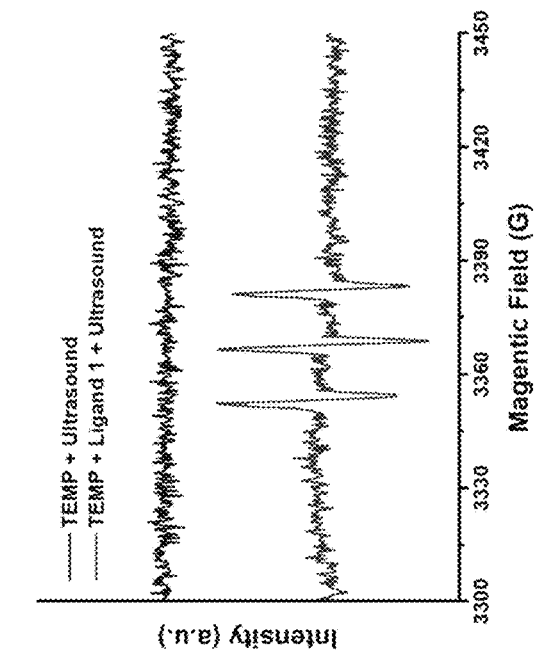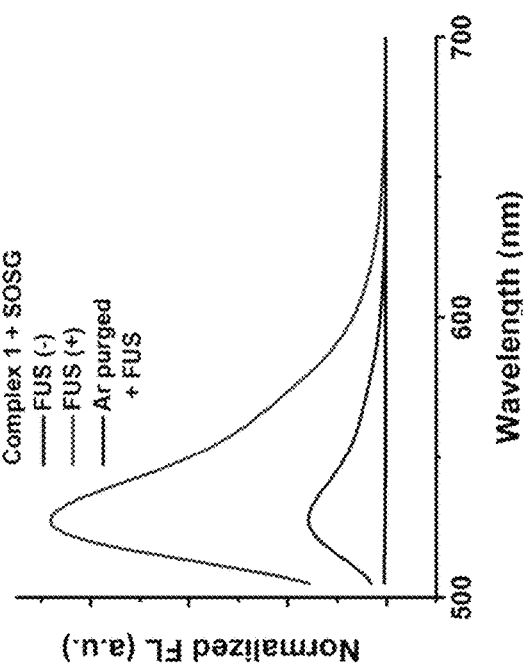
Fig. 7A
Fig. 7B
Fig. 7C

| Cell line | Carboplatin | Mixture[a] | Mixture + US | SI[b] | Complex 1 | Complex 1 + US | SI[c] |
|---|---|---|---|---|---|---|---|
| HeLa | >40 | >40 | >40 | >1 | 26.3±2.8 | 4.1±0.2 | 6.4 |
| MCF-7 | >40 | >40 | 8.8±0.6 | >4.5 | >40 | 4.2±0.3 | >9.5 |
| A2780 | >40 | >40 | 10.1±0.8 | >4.0 | >40 | 4.0±0.2 | >10.0 |
| A2780-cisR | >40 | >40 | 23.4±1.4 | >1.7 | >40 | 4.1±0.2 | >9.8 |
| RF[d] | | | 2.3 | | | 1.0 | |
| A549 | >40 | >40 | 6.6±0.7 | >6.1 | >40 | 3.5±0.5 | >11.4 |
| A549-cisR | >40 | >40 | 19.4±6.7 | >2.1 | >40 | 4.3±0.3 | >9.3 |
| RF | | | 2.9 | | | 1.2 | |
| 4T1 | >40 | >40 | 30.5±1.5 | >1.3 | >40 | 2.0±0.7 | >20 |

Fig. 9

RADIATION-ACTIVATABLE PLATINUM COMPLEX, ITS PREPARATION AND THERAPEUTIC USE

FIELD OF THE INVENTION

The present invention relates to a novel complex particularly but not exclusive to a radiation-activatable platinum complex. The present invention also relates to the preparation of the complex as well as the use of it in treating a disease, in particular, but not exclusive to a cancer.

BACKGROUND

Cancer remains a life-threatening disease affecting a steadily increasing number of people overall in the world. Among various types of cancer treatments, chemotherapy, particularly with the use of platinum-based chemodrugs appears to be most common since the discovery of antitumor activity of cisplatin in 1965. Whilst platinum-based chemodrugs have been widely applied in clinics, with over 50% of cancer patients receiving platinum-based chemodrugs alone or in combination with other therapeutic modalities (e.g. surgical ablation or radiotherapy), the therapeutic outcome of platinum-based chemodrugs usually suffers from numerous drawbacks including low bioavailability, severe side effects, poor stability, and inherent or acquired resistance.

It has been reported that Pt(IV)-based complexes are activatable by reductive elimination to release active products, namely, Pt(II) drugs, in cells. Since then, the development of Pt(IV)-based prodrug has attracted much attention, particularly the development of photoactivatable Pt(IV) prodrugs in view of their non-invasiveness and controllability. Such development, however, generally suffers from the problem of limited penetration of light into deep tumor sites, which, on the one hand reducing the efficacy of the Pt(IV) prodrug against deep tumor; on the other hand, it undermines the side effect associated with the retention of the inactivated prodrugs in the tissues.

An alternative non-invasive therapy, called sonodynamic therapy (SDT), is thus attracting increasing attention in view of its high tissue penetrative depth, high remote spatiotemporal selectivity and non-invasiveness. Similar to PDT, typical SDT involves a "three-component system", namely a sonosensitizer, molecular oxygen ($O_2$), and low-intensity ultrasound (US). Specifically, when the sonosensitizer is exposed to US with a specific frequency range in conjunction with molecular oxygen, reactive oxygen species (ROS) will be generated and causes tumor cell apoptosis and/or necrosis.

The single-mode of therapeutic approach, i.e. reliance on the generation and action of ROS against cancer cells, however, has made SDT limited application in cancer treatment as the effect of ROS may be countered by the intrinsic antioxidant defence mechanism of cancer cells.

Thus, there remains a strong need for new compounds with acceptable side effects that can be used as an alternative or alternatively in addition to other types of anticancer drugs or drug carriers for effectively treating cancer, including cancer with intrinsic or acquired chemoresistance.

SUMMARY OF THE INVENTION

In a first aspect of the present invention, there is provided a platinum complex comprising a structure of Formula (I):

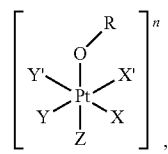

Formula (I)

wherein:
X, X', Y, Y' and Z are independently selected from the group consisting of ammonia, hydroxide, halide, oxalate, diamines, dicarboxylate, glycolate and —OR, optionally X and X' are linked to form a first bidentate ligand, and/or Y and Y' are linked to form a second bidentate ligand;
n is selected from the group consisting of zero, any positive charge, and any negative charge;
R is a radiation-responsive moiety having a structure of Formula (II):

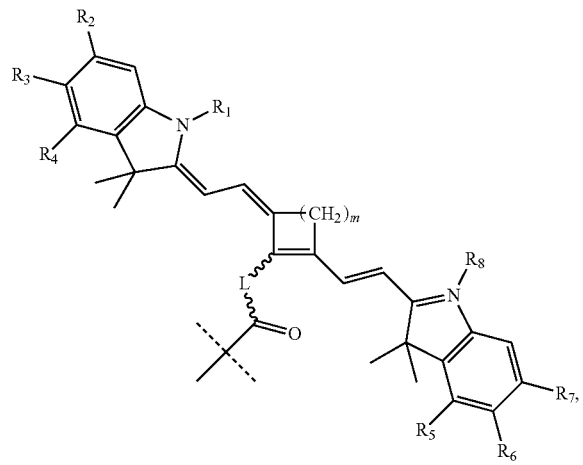

Formula (II)

with L being a linker group, m being 0 or a positive integer, $R_1$ to $R_8$ each being independently a substituent or a hydrogen, wherein an adjacent pair of $R_2$ to $R_7$ may form a fused heterocyclic or carbocyclic ring.

Preferably, L is a phenoxy-containing group, a thioether-containing group, or a secondary amine-containing group; m is 0, 2 or 3; $R_1$ and $R_8$ are independently selected from a linear or branched alkyl chain, a sulfonate-containing group, a carboxyl group, a carboxylate ester-containing group, or a heterocyclic group; and $R_2$ to $R_7$ are each independently selected from a hydrogen, a halogen, or an adjacent pair of $R_2$ to $R_7$ forming a fused 6-membered carbocyclic ring.

More preferably, L is selected from any one of the following groups:

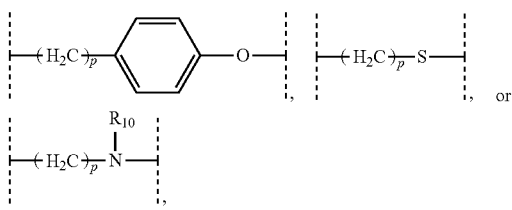

with p being 1-4, and $R_{10}$ being H, a linear or branched C1-C6 alkyl group, or a functional side chain; m is 0, 2 or 3; $R_1$ and $R_8$ are independently selected from a linear or branched alkyl chain, a sulfonate-containing group, a carboxyl group, a carboxylate ester-containing group, or a heterocyclic group; and $R_2$ to $R_7$ are each independently selected from a hydrogen, a halogen, or an adjacent pair of $R_2$ to $R_7$ forming a fused 6-membered carbocyclic ring.

It is preferred that Z is not —OR.

In a preferred embodiment, the platinum complex has a structure of Formula (III):

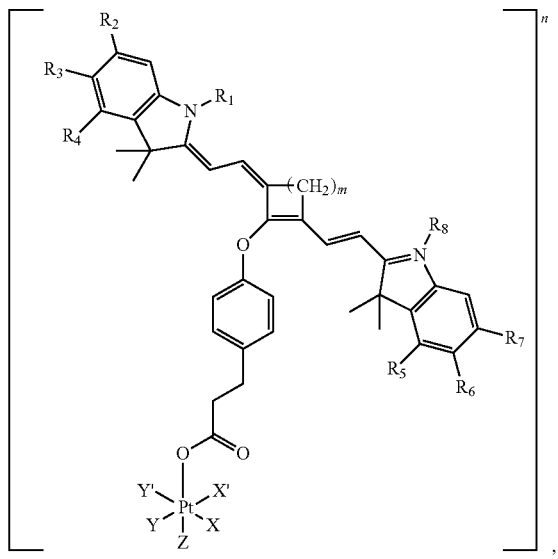

Formula (III)

with either X and X' or Y and Y' are linked to a bidentate ligand; and Z is hydroxide or —OR.

Preferably, X and X' are linked to form a dicarboxylate; Y and Y' are ammonia; and Z is hydroxide.

It is preferred that $R_1$ and $R_8$ are independently selected from —$CH_3$, —$(CH_2)_2CH_3$, —$(CH_2)_2COOH$, —$(CH_2)_5COOH$, —$(CH_2)_4SO_3H$,

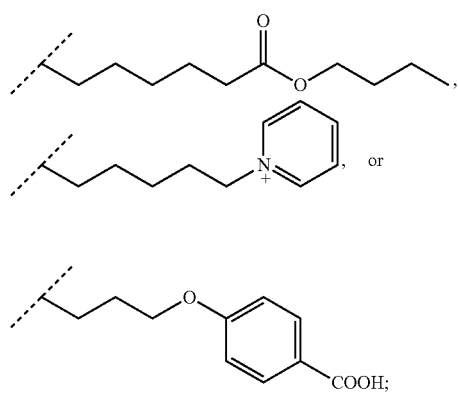

$R_2$ to $R_7$ are each independently selected from a hydrogen, chloride, iodide, bromide, or an adjacent pair of $R_2$ to $R_7$ are fused to form a benzene ring.

In a preferred embodiment, the platinum complex has a structure of Formula (IIIa):

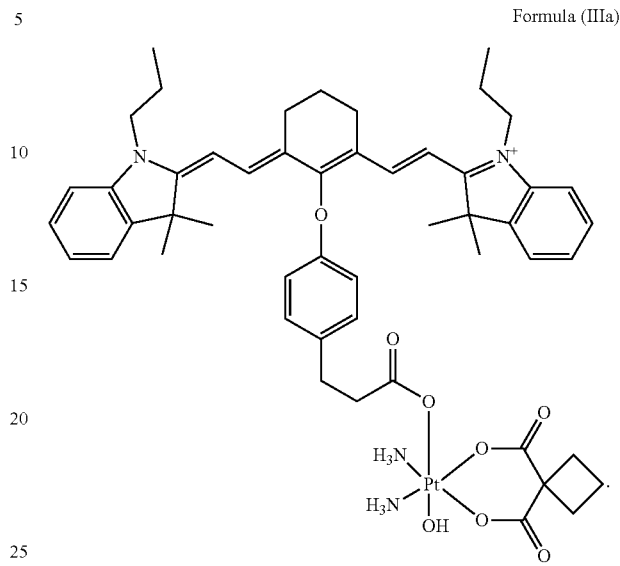

Formula (IIIa)

It is preferred that the chemical structure of the complex remains unchanged for at least about 6 hours in the absence of radiation.

Preferably, the complex is reducible to a reduced form and/or generates reactive oxygen species by exposure to radiation.

More preferably, the cytotoxicity of the complex is enhanced by at least about 6 times under the exposure to radiation.

In a second aspect of the present invention, there is provided a method of preparing the platinum complex in the first aspect, i.e. for preparing a platinum complex having a structure of Formula (I):

Formula (I)

with X, X', Y, Y' and Z, R as described herein.

The present invention in the third aspect provides a pharmaceutical composition comprising a platinum complex in the first aspect and further including a pharmaceutically acceptable carrier.

According to the fourth aspect of the invention, there is provided a method of treating a target tissue, comprising administering to a patient in need thereof a platinum complex in the first aspect and administering to the target tissue radiation in an amount and of a frequency effective to activate the complex.

In a preferred embodiment, the radiation is ultrasound. The ultrasound has a frequency between about 1 MHz to about 3 MHz. The ultrasound is applied at a power of about 1 W to about 4 W.

In a preferred embodiment, the radiation is light. The light has a frequency of between about 350 THz to about 500 THz. The light is applied at a power intensity from about 3 mW/cm$^2$ to about 350 mW/cm$^2$.

It is preferred that the target tissue is a tumor. Preferably, the tumor is selected from the group consisting of cervical cancer, lung cancer, ovarian cancer, breast cancer and mammary cancer.

In a preferred embodiment, the tumor has an intrinsic or acquired cisplatin-resistance.

In a preferred embodiment, the platinum complex acts as a prodrug.

In a fifth aspect of the present invention, there is provided a use of the platinum complex in the first aspect of the invention in preparation of a medicament for treating a target tissue by sonodynamic therapy, photodynamic therapy, chemotherapy and/or a combination thereof.

BRIEF DESCRIPTION OF THE DRAWINGS

FIG. 7A shows the fluorescent spectra of a mixture of ligand 1 and singlet oxygen sensor green (SOSG) under an ambient or degassed conditions with or without focused ultrasound (FUS) activation (4 W, 15 min) at 37° C.

FIG. 7B shows the fluorescent spectra of a mixture of complex 1 and singlet oxygen sensor green (SOSG) under an ambient or degassed conditions with or without focused ultrasound (FUS) activation (4 W, 15 min) at 37° C.

FIG. 7C shows the electroparamagnetic resonance spectra of a mixture of ligand 1 and 2,2,6,6-tetramethyl-piperidine (TEMP) in the presence of FUS activation (4 W, 15 min).

FIG. 9 is a table showing the IC$_{50}$ value (μM) of different cancer cell lines. $^a$Mixture: mixture of equivalent carboplatin and ligand 1. Drug feeding: 30 min, US condition: 3.5 W, 15 min, cell viability tested at 24 h post-treatment. $^b$Sono-sensitization Index (SI): defined by the IC$_{50}$ value for ultrasound activated mixture divided by the IC$_{50}$ value of the mixture without ultrasound activation. $^c$Sono-sensitization Index (SI): defined by the IC$_{50}$ value of ultrasound activated complex 1 divided by the IC$_{50}$ value of complex 1 without ultrasound activation. $^d$RF: defined by the IC$_{50}$ value of platinum-resistant cell lines (A2780cisR or A549cisR) divided by the IC$_{50}$ value of their original cell lines (A2780 or A549).

DESCRIPTION OF THE PREFERRED EMBODIMENTS

Figure 1:
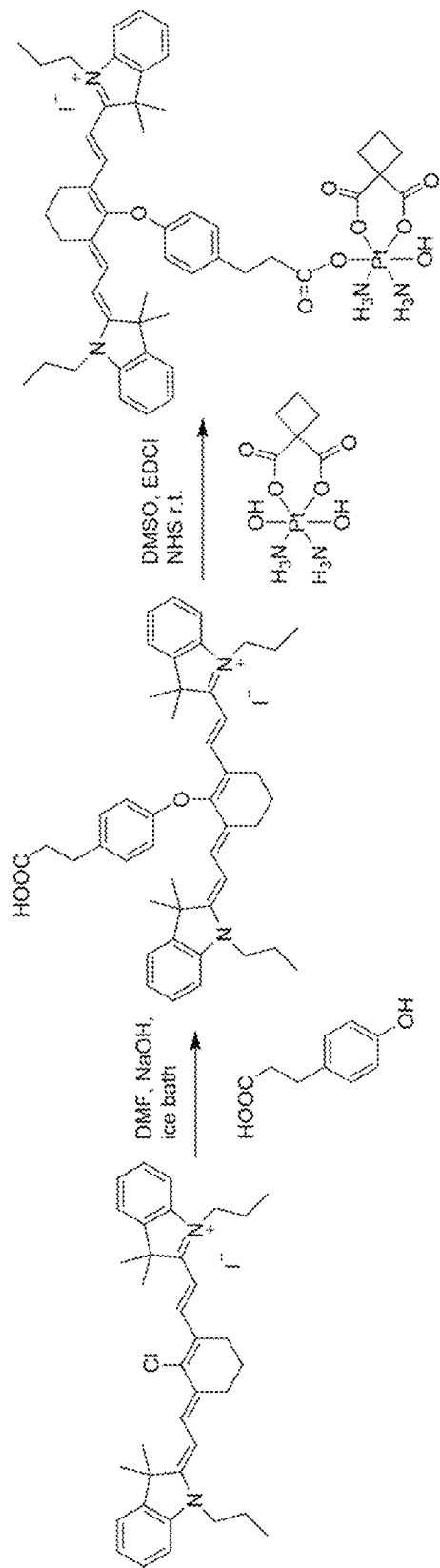
FIG. 1 shows a synthetic scheme of complex 1 (i.e. the platinum complex having a structure of Formula (IIIa)).

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

Unless otherwise defined, all technical terms used herein have the same meaning as commonly understood by one skilled in the art to which the invention belongs.

As used herein, the forms "a", "an", and "the" are intended to include the singular and plural forms unless the context clearly indicates otherwise.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Without intending to be limited by theory, the inventors have, through their own researches, trials, and experiments, devised a platinum complex that may be used as a prodrug for cancer treatment. In particular, the complex is activatable by radiation such as acoustic radiation, electromagnetic radiation, and/or the like, resulting in the release of an active, chemotherapeutic compound as well as generation of singlet oxygen ($^1O_2$) for synergistic therapy. In an example embodiment, the complex as described herein may be effectively reducing the proliferation of various types of cancer cell, including those with cisplatin-resistance upon radiation activation.

According to the invention, there is provided a platinum complex, particularly a platinum(IV) complex, comprising a structure of Formula (I):

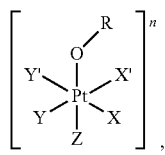

Formula (I)

wherein:
X, X', Y, Y' and Z are independently selected from the group consisting of ammonia, hydroxide, halide, oxalate, diamines, dicarboxylate, glycolate and —OR, optionally X and X' are linked to form a first bidentate ligand, and/or Y and Y' are linked to form a second bidentate ligand;
n is selected from the group consisting of zero, any positive charge, and any negative charge;
R is a radiation-responsive moiety having a structure of Formula (II):

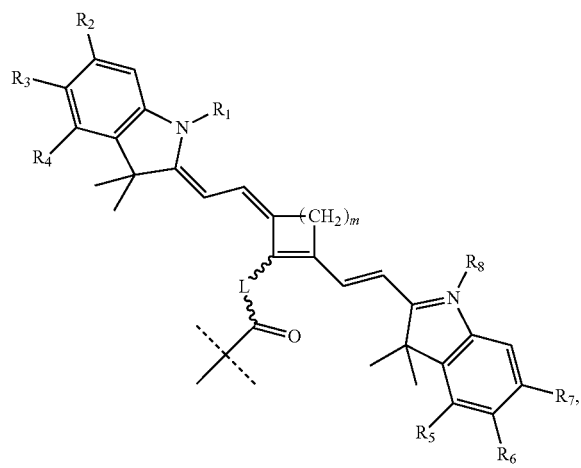

Formula (II)

with L being a linker group, m being 0 or a positive integer, $R_1$ to $R_8$ each being independently a substituent or a hydrogen, wherein an adjacent pair of $R_2$ to $R_7$ may form a fused heterocyclic or carbocyclic ring.

The term "radiation-responsive moiety" as used herein refers to a functional part of the platinum complex which can allow the platinum complex to generate reactive oxygen species (ROS) such as singlet oxygen ($^1O_2$) and can facilitate the reduction of the platinum complex to its reduced form such as a platinum(II) complex and the release thereof, in the presence of a reducing agent/reductant upon exposure to the radiation.

For example, upon exposure to the radiation, the radiation-responsive moiety may be excited to an excited state by absorption of such radiation and/or by other mechanism such as the micro-cavitation effect, which in turn bringing the overall platinum complex into an excited state. The excited platinum complex, when returning to its ground state, may generate $^1O_2$ via a Type II process through energy transfer with the molecular oxygen. Meanwhile, the generation of $^1O_2$ may facilitate the electron transfer process between the platinum complex and the reducing agent/reductant such as ascorbate, GSH and the like, thereby facilitating the reduction of the platinum complex into its reduced form and the release thereof.

The term "radiation" generally denotes the emission or transmission of energy in the form of waves through space or through a material medium. Examples of radiation may include electromagnetic (EM) radiation such as radio waves, microwaves, infrared, visible light, UV light, x-rays, gamma radiation and the like; and acoustic radiation such as ultrasound (US), sound and the like. In an embodiment, the radiation-responsive moiety is responsive to EM radiation particularly light such as infrared light. In another embodiment, the radiation-responsive moiety is responsive to acoustic radiation particularly US.

The linker group L is an organic unit of any length comprising atoms or groups to link, i.e., to connect, two parts of the platinum complex of the present invention, namely the "platinum part" of the platinum complex and the "radiation-responsive part" of the complex together. Examples of L may include phenoxy-containing group, a thioether-containing group, or a secondary amine-containing group. As used herein, the phrase "secondary" describes the amino group having two organic substituents, such as an alkyl group, an acryl group or both, bound to the nitrogen together with one hydrogen. In a particular embodiment, the linker group L may be an O-terminated, an N-terminated or an S-terminated linker. For example, the linker group L may be selected from any one of the following groups:

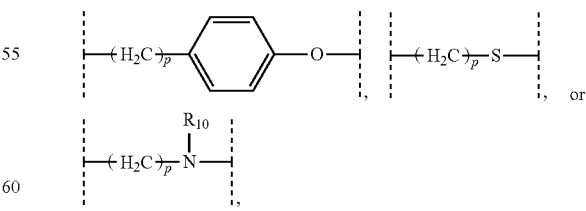

with p being 1-4, and $R_{10}$ being H, a linear or branched C1-C6 alkyl group, or a functional side chain. Examples of linear or branched C1-C6 alkyl group may include methyl, ethyl, n-propyl, isopropyl, n-butyl, isobutyl, sec-butyl, tert-butyl, n-pentyl, tert-pentyl, neopentyl, n-hexyl, and the like.

The term "functional side chain" as used herein denotes a compound or molecule, when bonded to the platinum complex of the present invention via the linker L, that may facilitate or enhance the biocompatibility, cellular accumulation, cellular uptake, ROS generation, chemical reduction of the platinum complex. Examples of the functional side chain may include PEG chains with a molecular weight such as from about 100 to about 5 k, cyclodextrins, biomolecules such as a penetrating protein, glycosides, fatty acids, biotin, folic acid and the like.

$R_1$ to $R_8$ are each independently a substituent or a hydrogen atom. The substituent can be, for example, a hydrocarbon group, a nitrogen-containing group, a heterocyclic group, an oxygen-containing group, a sulfur-containing group, a halogen or the like, wherein an adjacent pair of $R_2$ to $R_7$ may form a fused heterocyclic or carbocyclic ring. In a particular embodiment, $R_1$ and $R_8$ are independently selected from a linear or branched alkyl chain, a sulfonate-containing group, a carboxyl group, a carboxylate ester-containing group, or a heterocyclic group; and $R_2$ to $R_7$ are each independently selected from a hydrogen, a halogen, or an adjacent pair of $R_2$ to $R_7$ forming a fused 6-membered carbocyclic ring.

m is 0 or a positive integer such as 1, 2, 3, or 4. In a particular embodiment, m is 0, 2 or 3.

X, X', Y, Y' and Z are independently selected from the group consisting of ammonia, hydroxide, halide, oxalate, diamines, dicarboxylate, glycolate and —OR. X, X', Y, Y' and Z may optionally be linked to each other in any combination to form polydentate ligands, in particular bidentate ligands. The term "halide" generally denotes halide ions, in particular, including chloride, bromide, or fluoride.

In an embodiment, X and X' are linked to form a first bidentate ligand, and/or Y and Y' are linked to form a second bidentate ligand. In an embodiment, Z may be hydroxide or —OR. In another embodiment, Z may not be —OR.

n is selected from the group consisting of zero, any positive charge, and any negative charge. In an embodiment, n may be 0 or 1.

In a particular embodiment, the platinum complex has a structure of Formula (III):

Formula (III)

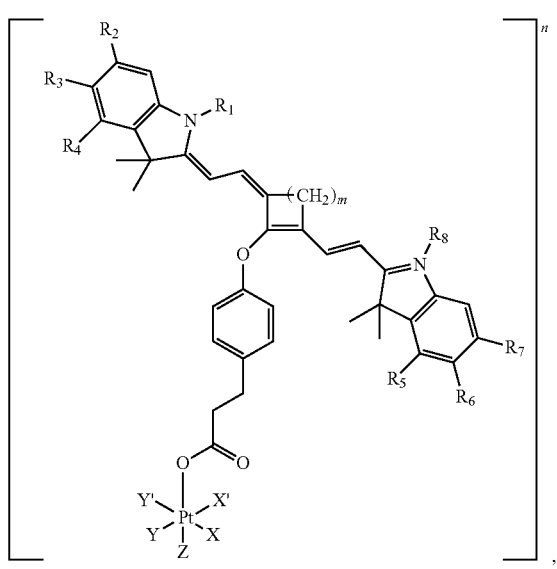

wherein:

X, X', Y, and Y' are independently selected from the group consisting of ammonia, hydroxide, halide, oxalate, diamines, dicarboxylate, glycolate and —OR, with either X and X' or Y and Y' are linked to a bidentate ligand; Z is hydroxide or —OR; and n, m, $R_1$ to $R_8$ are as defined above.

In particular, X and X' are linked to form a dicarboxylate; Y and Y' are ammonia (i.e. $NH_3$); Z is hydroxide; $R_1$ and $R_8$ are independently selected from —$CH_3$, —$(CH_2)_2CH_3$, —$(CH_2)_2COOH$, —$(CH_2)_5COOH$, —$(CH_2)_4SO_3H$,

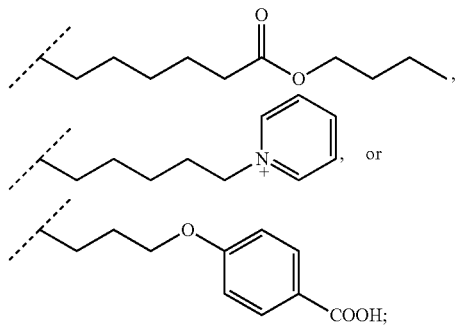

and $R_2$ to $R_7$ are each independently selected from a hydrogen, chloride, iodide, bromide, or an adjacent pair of $R_2$ to $R_7$ are fused to form a benzene ring.

As a specific embodiment, the platinum complex of the present invention may have a structure of Formula (IIIa):

Formula (IIIa)

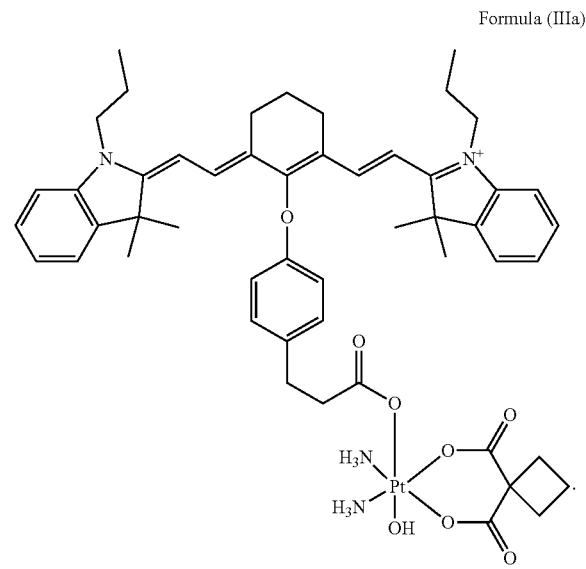

As mentioned herein, the platinum complex, particularly platinum(IV) complex, of the present invention may act as a prodrug for treating cancer. It is appreciated that one of the key factors for an effective prodrug is its stability prior to activation. In an example embodiment, the platinum complex of the present invention may remain intact prior activation but become cytotoxic towards cancer cells including platinum-resistant cancer cells upon activation. In particular, the chemical structure of the complex may remain unchanged for such as at least about 6 hours in the absence of radiation. In contrast, upon exposure to radiation, the platinum complex is reducible to a reduced form that is cytotoxic and generates reactive oxygen species particularly singlet oxygen. In an embodiment, the platinum complex, upon the exposure of radiation, may have an enhanced cytotoxicity of at least 6 times as compared with the platinum complex without being exposed to said radiation. In an example embodiment where the platinum complex may have a structure of Formula (III) such as Formula (IIIa), the cytotoxicity (in terms of $IC_{50}$ value, μM) of the complex towards, such as HeLa cells may be of about 26 μM (without exposure to radiation) and about 4 μM (with the exposure to radiation), respectively (i.e. the cytotoxicity of the platinum complex is enhanced by about 6 times upon the exposure to radiation).

A method of preparing the platinum complex is described below, i.e., for preparing a platinum complex having a structure of Formula (I):

Formula (I)

$$\left[ \begin{array}{c} Y' \\ Y \end{array} \!\!\!\! \begin{array}{c} O-R \\ | \\ Pt \\ | \\ Z \end{array} \!\!\!\! \begin{array}{c} X' \\ X \end{array} \right]^{n},$$

with X, X', Y, Y' and Z, n, R as defined herein.

The method comprises linking a platinum complex precursor which is in particular a platinum(IV) complex precursor comprising a structure of Formula (IV):

Formula (IV)

$$\left[ \begin{array}{c} Y' \\ Y \end{array} \!\!\!\! \begin{array}{c} OH \\ | \\ Pt \\ | \\ Z \end{array} \!\!\!\! \begin{array}{c} X' \\ X \end{array} \right]^{n'},$$

with a radiation-responsive moiety R to form the platinum complex as described herein, wherein X, X', Y, Y' and Z are as defined herein, n' means 0 (zero), any positive charge or any negative charge and wherein R has a structure of Formula (II):

Formula (II)

with L, m, $R_1$ to $R_8$ being defined herein.

The platinum complex(IV) complex precursor may particularly comprise a structure of Formula (IVa):

Formula (IVa)

$$\left[ \begin{array}{c} Y' \\ Y \end{array} \!\!\!\! \begin{array}{c} OH \\ | \\ Pt \\ | \\ OH \end{array} \!\!\!\! \begin{array}{c} X' \\ X \end{array} \right]^{n'},$$

i.e., Z is hydroxide.

In a particular embodiment, the platinum(IV) complex precursor may comprise a structure of Formula (V):

Formula (V)

In an embodiment of the present invention, the method is suitable for preparing a platinum complex having a structure of Formula (I) with R having a structure of Formula (II), i.e., a platinum complex having a structure of Formula (A):

Formula (A)

wherein:

X, X', Y, Y' and Z and n are as defined herein;

L is selected from any one of the following groups:

with p being 1-4, and $R_{10}$ being H, a linear or branched C1-C6 alkyl group, or a functional side chain as defined herein;

m is 0, 2 or 3;

$R_1$ and $R_8$ are independently selected from a linear or branched alkyl chain, a sulfonate-containing group, a carboxyl group, a carboxylate ester-containing group, or a heterocyclic group; and $R_2$ to $R_7$ are each independently selected from a hydrogen, a halogen, or an adjacent pair of $R_2$ to $R_7$ forming a fused 6-membered carbocyclic ring.

The method comprises the steps of:
i) optionally preparing a hydroxysuccinimide (NHS)-ester of a precursor compound having a part of the structure of Formula (II);
ii) reacting a platinum complex precursor of Formula (IV) such as Formula (IVa) or in particular of Formula (V) with the NHS-ester; and
iii) isolating the platinum complex of Formula (A) and optionally purifying the platinum complex.

The precursor compound may have a structure of Formula (VI), Formula (VII), or Formula (VIII):

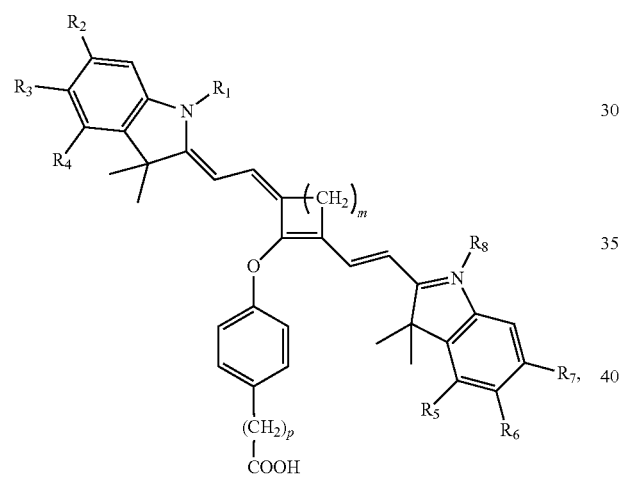

Formula (VI)

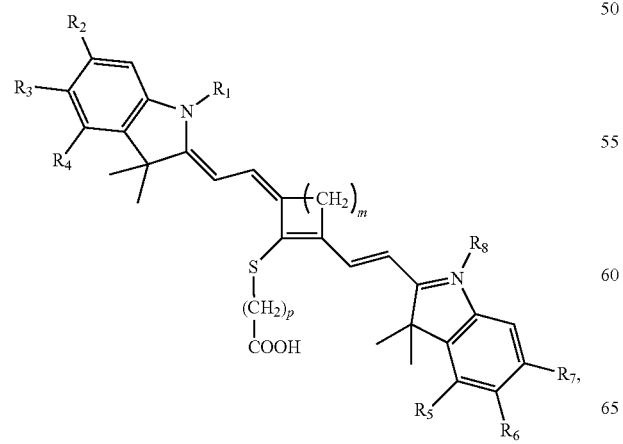

Formula (VII)

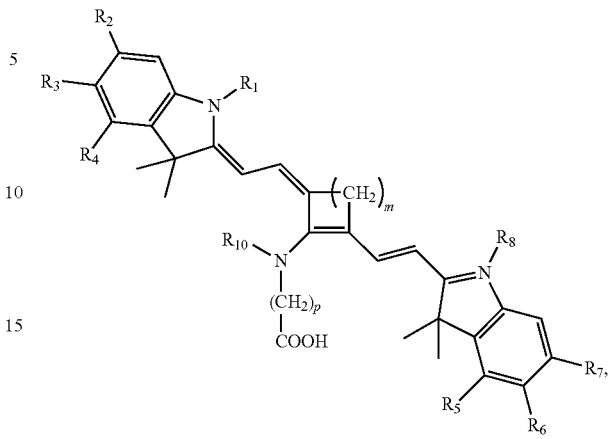

Formula (VIII)

with m, p and $R_{10}$ as defined herein.

Step i) in particular comprises:
a) reacting a polymethine dye, particularly a heptamethine cyanine dye with a linker precursor having a structure of Formula (IX), Formula (X) or Formula (XI) to form the precursor compound:

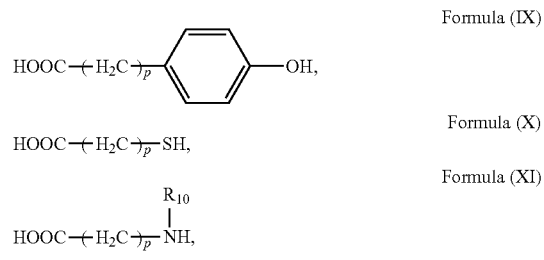

with p and $R_{10}$ as defined herein;
b) isolating the precursor compound and optionally purifying the precursor compound.

The heptamethine cyanine dye may comprise a structure of Formula (XII),

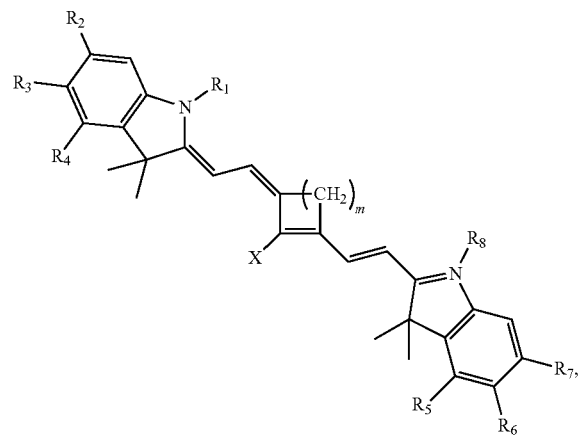

Formula (XII)

with $R_1$ and $R_8$ are independently selected from a linear or branched alkyl chain, a sulfonate-containing group, a carboxyl group, a carboxylate ester-containing group, or a heterocyclic group;

$R_2$ to $R_7$ are each independently selected from a hydrogen, a halogen, or an adjacent pair of $R_2$ to $R_7$ forming a fused 6-membered carbocyclic ring; and X being a halogen, particularly Cl, Br or I.

The reaction of step ia) may be carried out in a reaction solvent such as DMF under an alkaline condition such as with the presence of NaOH under room temperature. The reaction may be carried out for at least about 1 hour.

Step ii) particularly comprises:
a) preparing a mixture of the platinum complex precursor and the NHS-ester in a reaction solvent;
b) stirring the mixture after step a) for at least about 8 hour at a temperature of at least about 20° C.

The reaction solvent in step iia) is preferably dimethyl sulfoxide (DMSO). Optionally, the NHS-ester may be added in step iia) in form of a mixture with at least part of the reaction solvent, in particular DMSO.

The expressions "isolating the platinum complex" or "isolating the precursor compound" mean at least partially separating the platinum complex or the precursor compound from other components in the reaction mixture after step ib) or step ii). Step ib) or step iii) in particular comprises filtering the mixture for obtaining a filtrate, subjecting the mixture to centrifugation, allowing the platinum complex or the precursor compound to form precipitate in water such as cold water, adding a precipitation solvent to the filtrate for obtaining a precipitate and washing the precipitate with a washing solvent.

The purification step in step iii) and step ib) may be conducted by way of column chromatography such as silica-gel column chromatography, recrystallization and/or the like.

The method as described is suitable for preparing a platinum complex having a structure of Formula (III):

Formula (III)

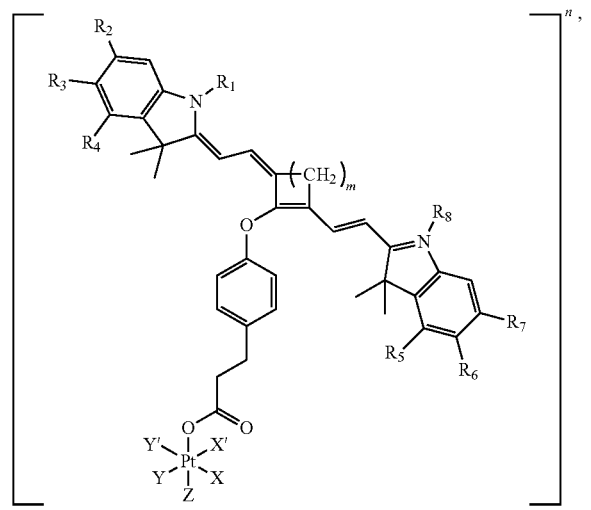

with X, X', Y, Y' and Z are independently selected from the group consisting of ammonia, hydroxide, halide, oxalate, diamines, dicarboxylate, glycolate and —OR, preferably either X and X' or Y and Y' are linked to form a bidentate ligand, and Z is hydroxide or —OR, or more preferably X and X' are linked to form a dicarboxylate; Y and Y' are ammonia; and Z is hydroxide.

$R_1$ and $R_8$ are independently selected from —$CH_3$, —$(CH_2)_2CH_3$, —$(CH_2)_2COOH$, —$(CH_2)_5COOH$, —$(CH_2)_4SO_3H$,

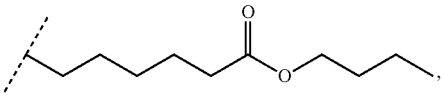

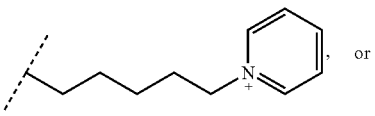, or

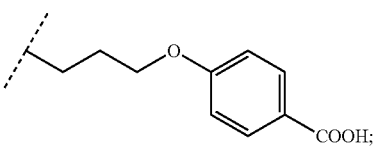

and $R_2$ to $R_7$ are each independently selected from a hydrogen, chloride, iodide, bromide, or an adjacent pair of $R_2$ to $R_7$ are fused to form a benzene ring.

As a specific embodiment, the method is suitable for preparing a platinum complex, in particular, a radiation-activatable platinum complex having a structure of Formula (IIIa):

Formula (IIIa)

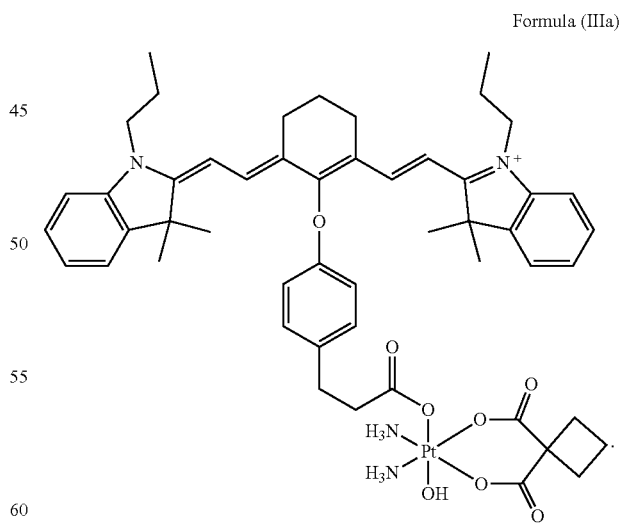

Another aspect of the invention relates to a pharmaceutical composition comprising a platinum complex of the present invention as described herein and a pharmaceutically acceptable carrier.

The platinum complex in the pharmaceutical composition may comprise a structure of Formula (I), in particular of Formula (A):

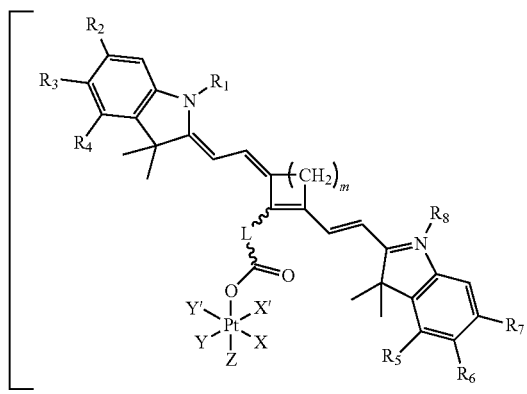

Formula (A)

with X, X', Y, Y' and Z and n as defined herein;
L is selected from any one of the following groups:

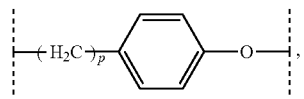

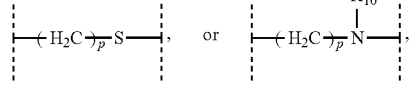

with p being 1-4, and $R_{10}$ being H, a linear or branched C1-C6 alkyl group, or a functional side chain as defined herein;

m is 0, 2 or 3;

$R_1$ and $R_8$ are independently selected from a linear or branched alkyl chain, a sulfonate-containing group, a carboxyl group, a carboxylate ester-containing group, or a heterocyclic group; and $R_2$ to $R_7$ are each independently selected from a hydrogen, a halogen, or an adjacent pair of $R_2$ to $R_7$ forming a fused 6-membered carbocyclic ring.

In an embodiment, the platinum complex in the pharmaceutical composition may comprise a structure of Formula (III):

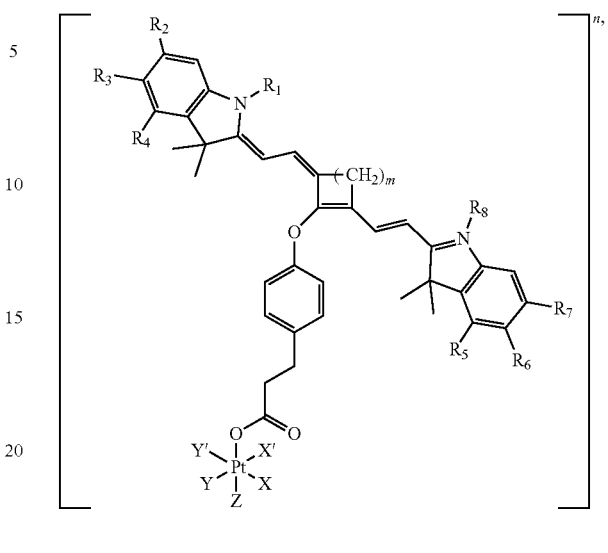

Formula (III)

with X, X', Y, Y' and Z are independently selected from the group consisting of ammonia, hydroxide, halide, oxalate, diamines, dicarboxylate, glycolate and —OR, preferably either X and X' or Y and Y' are linked to form a bidentate ligand, and Z is hydroxide or —OR, or more preferably X and X' are linked to form a dicarboxylate; Y and Y' are ammonia; and Z is hydroxide;

$R_1$ and $R_8$ are independently selected from —$CH_3$, —$(CH_2)_2CH_3$, —$(CH_2)_2COOH$, —$(CH_2)_5COOH$, —$(CH_2)_4SO_3H$,

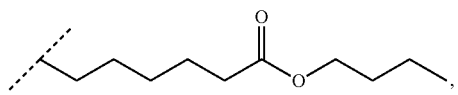

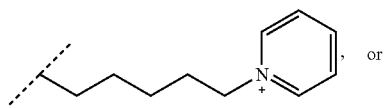

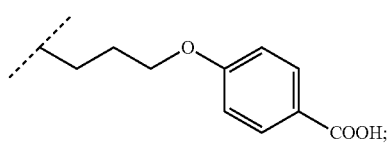

and $R_2$ to $R_7$ are each independently selected from a hydrogen, chloride, iodide, bromide, or an adjacent pair of $R_2$ to $R_7$ are fused to form a benzene ring.

More preferably, the platinum complex in the pharmaceutical composition may comprise a structure of Formula (IIIa):

Formula (IIIa)

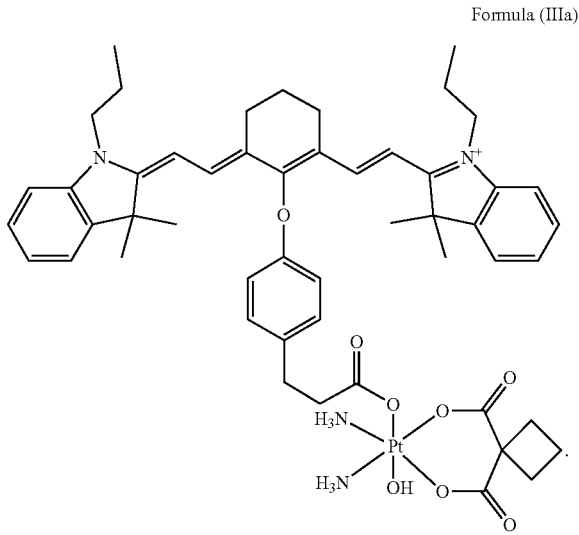

"Pharmaceutically acceptable carrier" are those that can facilitate the cellular uptake of the active ingredient and can be taken by a patient without therapeutically relevant adverse effects or negative influence in the efficiency of the complex. The pharmaceutical composition can be present in solid, semisolid or liquid form to be administered orally or via a parenteral route to the patient.

The present invention further relates to a method of treating a target tissue, comprising administering to a patient in need thereof a platinum complex as described above and administering to the target tissue radiation in an amount and of a frequency effective to activate the complex.

The term "target tissue" covers the site with cancer cells, cancerous tissues and any parts in proximity to the cancer cells or cancerous tissues of a patient in need of treatment. The target tissue may be located topically or inside the body of the patient. After the step of administering the complex to the patient for a specific period of time, with the target tissue being pre-located, an effective amount of radiation with effective frequency is applied to the target tissue to activate the complex that is at the site.

In an embodiment, the target tissue may be a tumor, in particular cancer. The term "tumor" or "tumorous" as referred herein describes an abnormal mass of tissue in a physiological condition in subjects (e.g. a patient), which may be benign, premalignant or malignant (cancerous) which may occur in any part of the body of a patient including solid tissue such as organ, muscle, bone and the like.

The terms "cancer" and "cancerous" describe a physiological condition in subjects (e.g. a patient) in which a population of cells are characterized by unregulated malignant (cancerous) cell growth. The cancer may or may not be drug-resistant cancer. The expression "drug-resistant cancer" generally denotes cancer that has a natural, i.e. intrinsic, or acquired resistance against one or more chemotherapeutic compounds in particular which has a natural or has an acquired, i.e. developed resistance against known coordination complexes of platinum such as cisplatin. A cancer is resistant against one or more chemotherapeutic compounds if it comprises cancer cells that are resistant against said chemotherapeutic compounds. Accordingly, the cancer cells with a resistant phenotype will be less sensitive or more tolerant to one or more chemotherapeutic compounds. Such cancer or cancer cells can be detected for example, by means of an MTT assay.

In the preferred embodiment, the platinum complex is used against malignant tumors in a patient who is diagnosed with cervical cancer, lung cancer, ovarian cancer, breast cancer, or mammary cancer, including cisplatin-resistant phenotype thereof.

The Resistant Factor of the platinum complex of the present invention towards cisplatin-resistant cancer cells is preferably less than 10, more preferably less than 8 and in particular even less than 5. The Resistant Factor is calculated by dividing the $IC_{50}$ of the platinum complex towards cisplatin-resistant cells by its $IC_{50}$ towards cancer cells of the same cell type or tissue which do not have a cisplatin-resistant phenotype.

In an alternative embodiment, the complex may be used against target tissue that is affected by an infection, in particular by bacteria infection, such as but not limited to *Staphylococcus aureus* and *Escherichia coli* infection.

The administered platinum complex may comprise a structure of Formula (I), particularly Formula (A):

Formula (A)

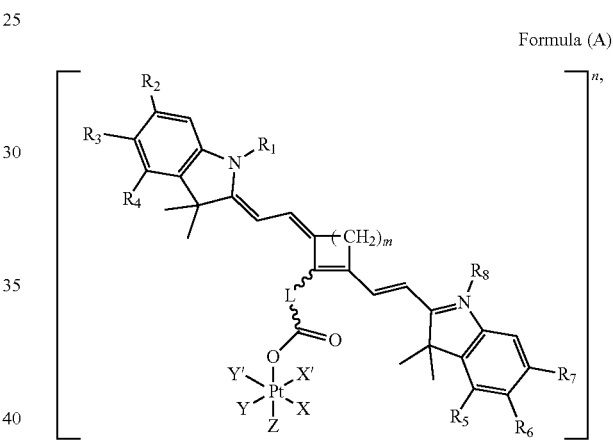

with X, X', Y, Y' and Z and n as defined herein;
L is selected from any one of the following groups:

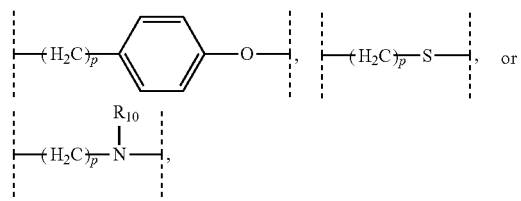

with p being 1-4, and $R_{10}$ being H, a linear or branched C1-C6 alkyl group, or a functional side chain as defined herein;

m is 0, 2 or 3;

$R_1$ and $R_8$ are independently selected from a linear or branched alkyl chain, a sulfonate-containing group, a carboxyl group, a carboxylate ester-containing group, or a heterocyclic group; and $R_2$ to $R_7$ are each independently selected from a hydrogen, a halogen, or an adjacent pair of $R_2$ to $R_7$ forming a fused 6-membered carbocyclic ring.

Preferably, the administered platinum complex may comprise a structure of Formula (III):

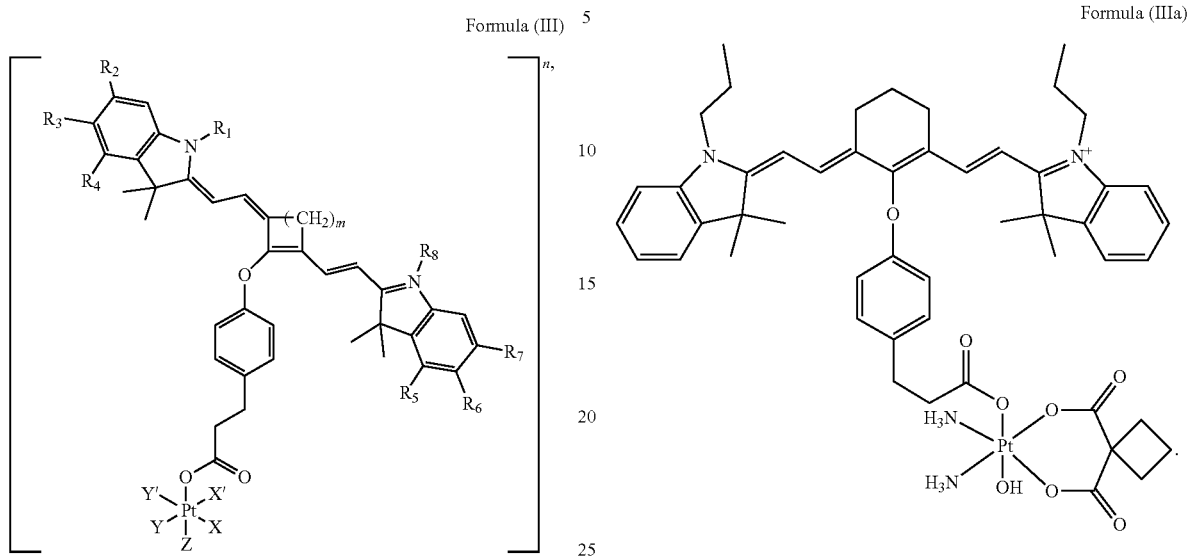

Formula (III)

with X, X', Y, Y' and Z are independently selected from the group consisting of ammonia, hydroxide, halide, oxalate, diamines, dicarboxylate, glycolate and —OR, preferably either X and X' or Y and Y' are linked to form a bidentate ligand, and Z is hydroxide or —OR, or more preferably X and X' are linked to form a dicarboxylate; Y and Y' are ammonia; and Z is hydroxide;

$R_1$ and $R_8$ are independently selected from —$CH_3$, —$(CH_2)_2CH_3$, —$(CH_2)_2COOH$, —$(CH_2)_5COOH$, —$(CH_2)_4SO_3H$,

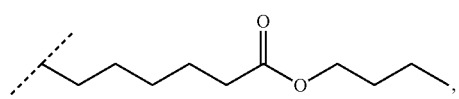,

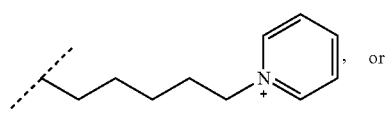, or

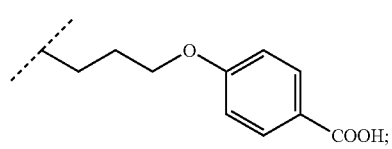;

and $R_2$ to $R_7$ are each independently selected from a hydrogen, chloride, iodide, bromide, or an adjacent pair of $R_2$ to $R_7$ are fused to form a benzene ring.

More preferably, the administered platinum complex may comprise a structure of Formula (IIIa):

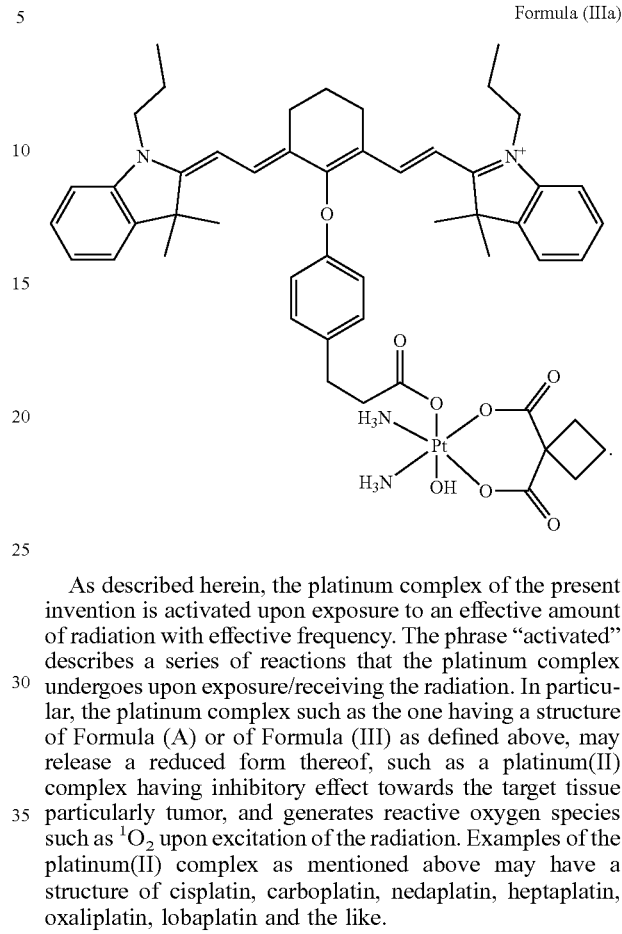

Formula (IIIa)

As described herein, the platinum complex of the present invention is activated upon exposure to an effective amount of radiation with effective frequency. The phrase "activated" describes a series of reactions that the platinum complex undergoes upon exposure/receiving the radiation. In particular, the platinum complex such as the one having a structure of Formula (A) or of Formula (III) as defined above, may release a reduced form thereof, such as a platinum(II) complex having inhibitory effect towards the target tissue particularly tumor, and generates reactive oxygen species such as $^1O_2$ upon excitation of the radiation. Examples of the platinum(II) complex as mentioned above may have a structure of cisplatin, carboplatin, nedaplatin, heptaplatin, oxaliplatin, lobaplatin and the like.

For example, in an embodiment where the platinum complex comprises a structure of Formula (III) in particular of Formula (IIIa), upon excitation by the radiation, the radiation-responsive moiety and therefore the platinum(IV) complex is excited to an excited state. When the platinum (IV) complex returns to the ground state, it will generate $^1O_2$ via a Type II process, which involves an energy transfer between the excited complex and molecular oxygen. Subsequently or simultaneously, the generation of $^1O_2$ (i.e. the reaction between the excited complex and molecular oxygen) would facilitate the electron transfer between the excited platinum(IV) complex and reducing agent(s) such as a cellular reducing agent including, for example, ascorbate, GSH, and the like, resulting in the release of a reduced form of the platinum(IV) complex, such as a platinum(II) complex particularly a platinum(II) complex having a structure of Formula (XIII):

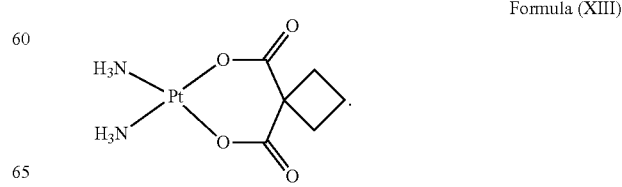

Formula (XIII)

Accordingly, the platinum complex of the present invention may act as a prodrug to release the active part such as the complex of Formula (XIII) for achieving the therapeutic effect and/or results in synergistic effect by the products (e.g. $^1O_2$) formed after radiation excitation.

The mechanism of the excitation as mentioned above may depend on the type of radiation applied to the platinum complex. For example, in an embodiment where the radiation is acoustic radiation particularly ultrasound, the platinum complex may be excited by the micro-cavitation effect; whereas in another embodiment where the radiation is electromagnetic radiation particularly light such as UV light, infrared light and the like, the platinum complex may be excited by following some general principles of photochemistry, such as but not limiting to the first law of photochemistry and the second law of photochemistry, etc.

The amount of the complex to be administered depends on the species, body weight, age and individual conditions of the patient and can be determined by standard procedures such as with cell cultures or experimental animals. An effective amount or concentration of the complex, for example, may be at least about 1 µg/mL.

The complex can be present in solid, semisolid or liquid form. Depending on the form the complex to be present, the complex may be administered by an oral, topical, intravenous or parenteral route to the patient in need thereof, preferably by an oral route or an intravenous route.

The expressions "effective amount", "effective dose", and "effective frequency" generally denote an amount of radiation or a particular range or specific frequency sufficient to activate the complex of the present invention that is located in the target tissue, so as to produce therapeutically desirable results, wherein the exact nature of the result varies depending on the specific disorder which is treated. When the disorder involves a tumor, in particular cancer, the result is usually an inhibition or suppression of the proliferation of the cancer cells, a reduction of cancerous cells or the amelioration of symptoms related to the cancer cells. When the disorder is a bacteria infection, the result is the inhibition or suppression of the proliferation of the bacteria, a reduction of bacteria colony or the amelioration of symptoms related to the bacteria infection.

In particular, the "effective amount", "effective dose", and "effective frequency" of the administered radiation may be sufficient and/or can be absorbed by and/or exciting the radiation-responsive moiety of the complex to an excited state for subsequent chemical reactions as detailed above, allowing the complex to generate ROS, particularly $^1O_2$ via Type-II mechanism and to release an active, reduced form of the complex, such as a platinum(II) complex as described above (i.e. activating the complex). The generated ROS and the released platinum(II) complex may therefore act on the cancer cells, leading to at least an inhibition or suppression of the proliferation thereof.

As described herein, inhibiting the growth/proliferation of cancer cells (or bacteria) can mean a decrease in the cell (or bacteria) viability in particular a significant decrease and/or an increase in the number of apoptotic cells (or colony forming unit (CFU) for bacteria), in particular a significant increase. The skilled person is aware of methods for verifying such effects. For cancer cells, methods such as with cell viability measurement by means of a MTS proliferation assay, a MTT assay, a live/dead cell co-staining viability assay (Calcein-AM/PI), or by determination of the apoptosis rate by means of Annexin V flow cytometry measurement. For bacteria, standard colony counting method known in the art may be used, such as by means of determining bacteria inhibition rate (IR) using, for instance, Formula (1):

$$IR = \frac{C_0 - C}{C_0} \times 100\%, \qquad \text{Formula (1)}$$

where C is the number of colony forming units (CFU) of the experimental group, and $C_0$ is the number of CFU of the control group.

As used herein, the term "significant" means that is statistically significant as determined by Student's t-test or other art-accepted measures of statistical significance.

The effective frequency as described herein may depend on the type of radiation administered. In an embodiment where the radiation is ultrasound, the effective frequency may be from about 1 MHz to about 3 MHz, from about 1.05 MHz to about 3.05 MHz, from about 0.95 MHz to about 2.95 MHz, from about 1.25 MHz to about 3 MHz, from about 1.25 MHz to about 2.75 MHz, from about 1.5 MHz to about 3 MHz, from about 1.75 MHz to about 3 MHz, or from about 1.75 MHz to about 2.5 MHz. In a specific embodiment of the present invention, the ultrasound is applied to the target area at a frequency of about 1.75 MHz.

In an embodiment where the radiation is light, the effective frequency may be from about 350 THz to about 500 THz, from about 355 THz to about 505 THz, from about 345 THz to about 500 THz, from about 345 THz to about 505 THz, from about 360 THz to about 500 THz, or from about 370 THz to about 500 THz. In a specific embodiment of the present invention, the light is applied to the target area at a frequency of about 370 THz.

It is appreciated that a person skilled in the art would be able to convert the frequency (f) of light to wavelength (λ) by Formula (2):

$$\lambda = \upsilon \times f \qquad \text{Formula (2)}$$

where υ is speed of light in vacuum, i.e., 299,792,458 m/s.

For example, in embodiment where the frequency is about 370 THz, the equivalent wavelength would be about 810 nm.

The effect amount of administered radiation may be measured in terms of power or power intensity, and the exact amount thereof may depend on the type of radiation administered. In an embodiment where the radiation is ultrasound, the effect amount ultrasound is measured in terms of power, which may be from about 1 W to about 4 W, from about 1.5 W to about 4 W, from about 1 W to about 3.5 W, from about 1.5 W to about 3.5 W, from about 2 W to about 4 W, or from about 3 W to about 4 W.

In an embodiment where the radiation is light, the effective amount of light is measured in terms of power intensity, which may be from about 3 mW/cm$^2$ to about 350 mW/cm$^2$, from about 2.9 mW/cm$^2$ to about 350 mW/cm$^2$, from about 3 mW/cm$^2$ to about 355 mW/cm$^2$, from about 3.2 mW/cm$^2$ to about 350 mW/cm$^2$, from about 3.3 mW/cm$^2$ to about 350 mW/cm$^2$, or from about 3.3 mW/cm$^2$ to about 348 mW/cm$^2$.

It is appreciated that, optionally or additionally, the method may be performed in combination with other therapeutically effective treatments such as one or more of:

i) treatment involving other therapeutically effective compounds such as chemotherapeutic compounds including, for example, a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog;

ii) radiation therapy; and/or iii) hormonal therapy.

The complex, in particular of the complex having a structure of Formula (A), such as Formula (III) or Formula (IIIa) is suitable for or specifically designed for use as a medicament for the treatment of target tissue or is suitable for or specifically designed for use in the preparation of a medicament for treatment of the target tissue by sonodynamic therapy, photodynamic therapy, chemotherapy and/or a combination thereof as described herein. In an embodiment, the target tissue may be a tumor, in particular a cancer as defined above. In another embodiment, the target tissue may be affected by infection, in particular by bacteria infection, as defined above.

The medicament comprises the complex in particular the complex having a structure of Formula (A), Formula (III), or Formula (IIIa) as described herein, and a pharmaceutically acceptable carrier as defined herein.

The medicament may be of various forms, such as in oral or in injection form, depending on the administration method and using various conventionally used methods for preparing a medicament. Examples of oral formulations may include tablets, powders, granules, capsules, pills, lozenges, solutions, syrups, elixirs, emulsions, oily or aqueous suspensions, and so forth.

Examples of solid formulations include tablets, powders, granules, capsules, pills, and lozenges. These solid formulations may contain pharmaceutically acceptable additives together with a crystal of the present invention. Examples of additives include fillers, extenders, binders, disintegrating agents, dissolution promoting agents, skin wetting agents, and lubricants, and these can be selected and mixed as required to prepare a medicament.

Examples of liquid formulations include solutions, syrups, elixirs, emulsions, and suspensions. These liquid formulations may contain pharmaceutically acceptable additives together with a crystal of the present invention. Examples of additives include suspending agents and emulsifiers, and these are selected and mixed as required to prepare a formulation.

EXAMPLES

Materials and Reagents Used

All materials were purchased from commercial sources and used as received without further purification. Unless specified, all the reactions were carried out in the dark.

Instrumentation and Characterization

The NMR data were recorded with a Bruker AVANCE III 300/400 MHz spectrometer or a Bruker Ascend AVANCE III 600 MHz spectrometer at room temperature. The ESI-MS data were recorded with a Liquid Chromatograph-Mass Spectrometer (API-3200 Triple-Q MS/MS). Analytical HPLC was conducted on a Shimadzu Prominence LC-20AT HPLC system, with a reversed-phase C18 column (Phenomenex Garmin 250×4.60 mm, 5 µm, 110 Å) (RP-HPLC). The photometric diode array (PDA) detector was applied to scan the absorption spectrum from 190-800 nm. Solvent A ($H_2O$ with 5% ACN) and solvent B (ACN with 5% $H_2O$) were used for a gradient elution at a flow rate of 1.0 mL $min^{-1}$. The test samples were eluted following the program: 5% B (0 min)→20% B (7 min)→90% B (16 min)→90% B (25 min). Pt content was measured by an Inductively Coupled Plasma-Optical Emission Spectrometer (ICP-OES) (PE Optima 8000).

Example 1

Preparation of Complex 1

Complex 1 of the present invention (i.e., the platinum complex of Formula (IIIa) of the present invention, cyaninplatin) was prepared according to reaction scheme as shown in FIG. 1. The reaction begins with the synthesis of ligand 1, followed by converting ligand 1 into an NHS-ester and subsequently or in situ reacting with a platinum complex precursor to obtain complex 1.

Figure 2A:
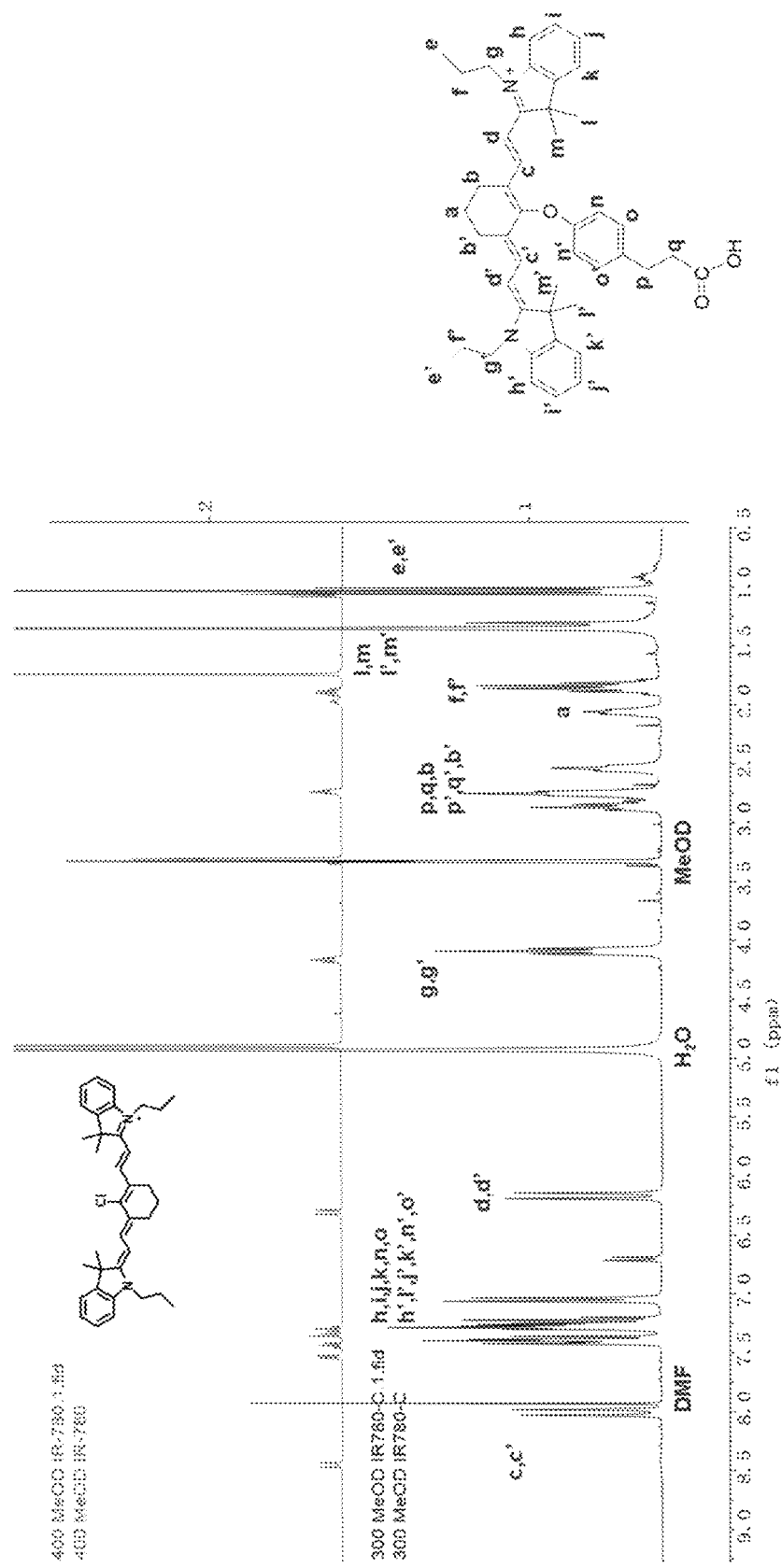
FIG. 2A shows a $^1$H nuclear magnetic resonance (NMR) spectrum of commercially available IR780 (upper) and ligand 1 (lower) prepared in an embodiment of the present invention.
Figure 2B:
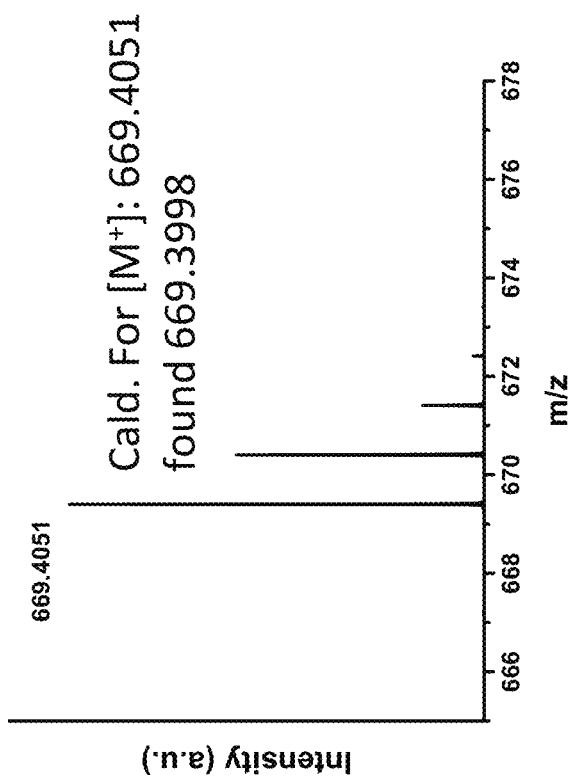
FIG. 2B shows a high-resolution mass spectroscopy (HR-MS) spectrum of ligand 1 prepared in an embodiment of the present invention.
Figure 3A:
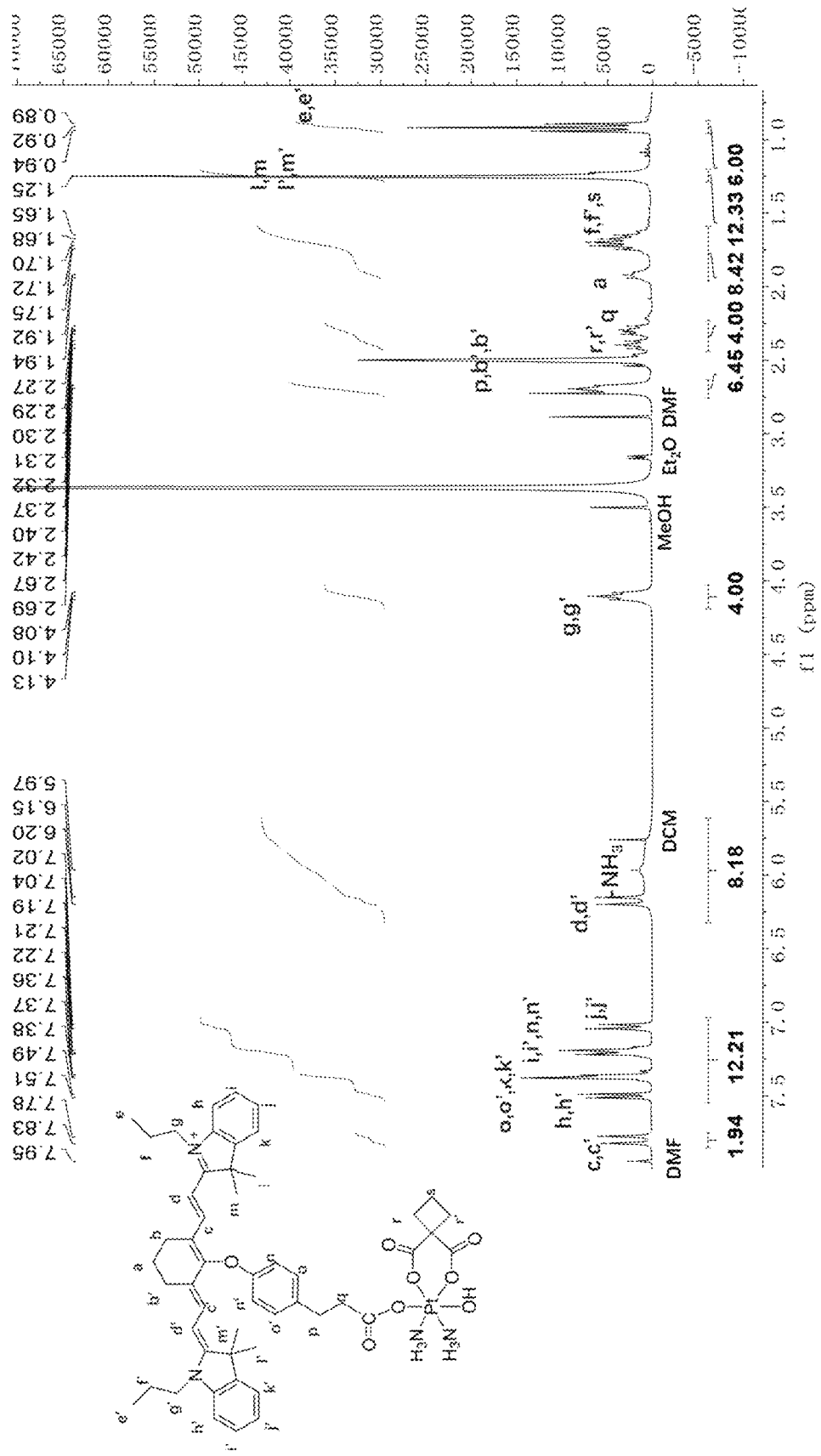
FIG. 3A shows a $^1$H NMR spectrum of complex 1 prepared in an embodiment of the present invention.
Figure 3B:
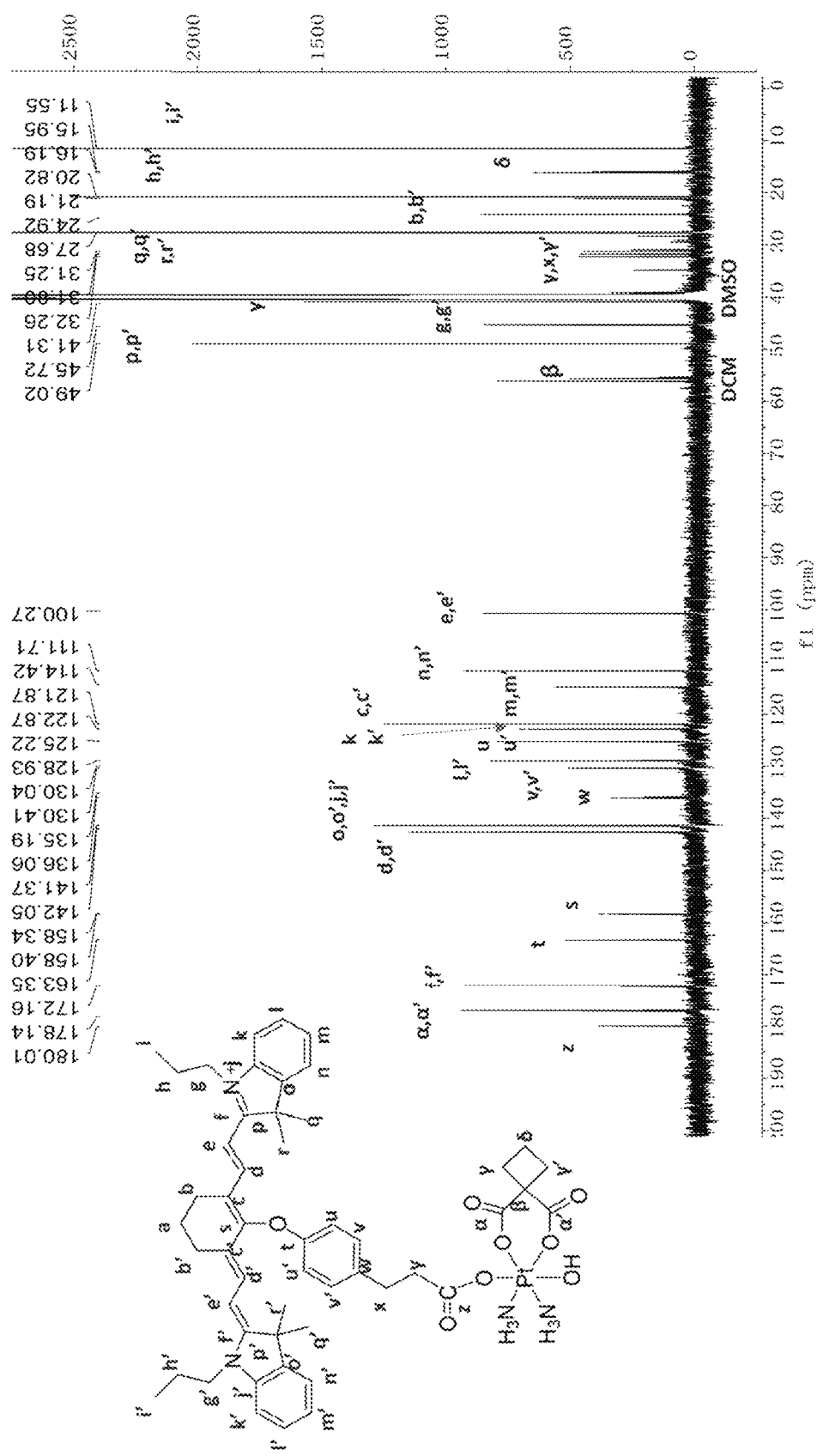
FIG. 3B shows a $^{13}$C NMR spectrum of complex 1 prepared in an embodiment of the present invention.
Figure 3C:
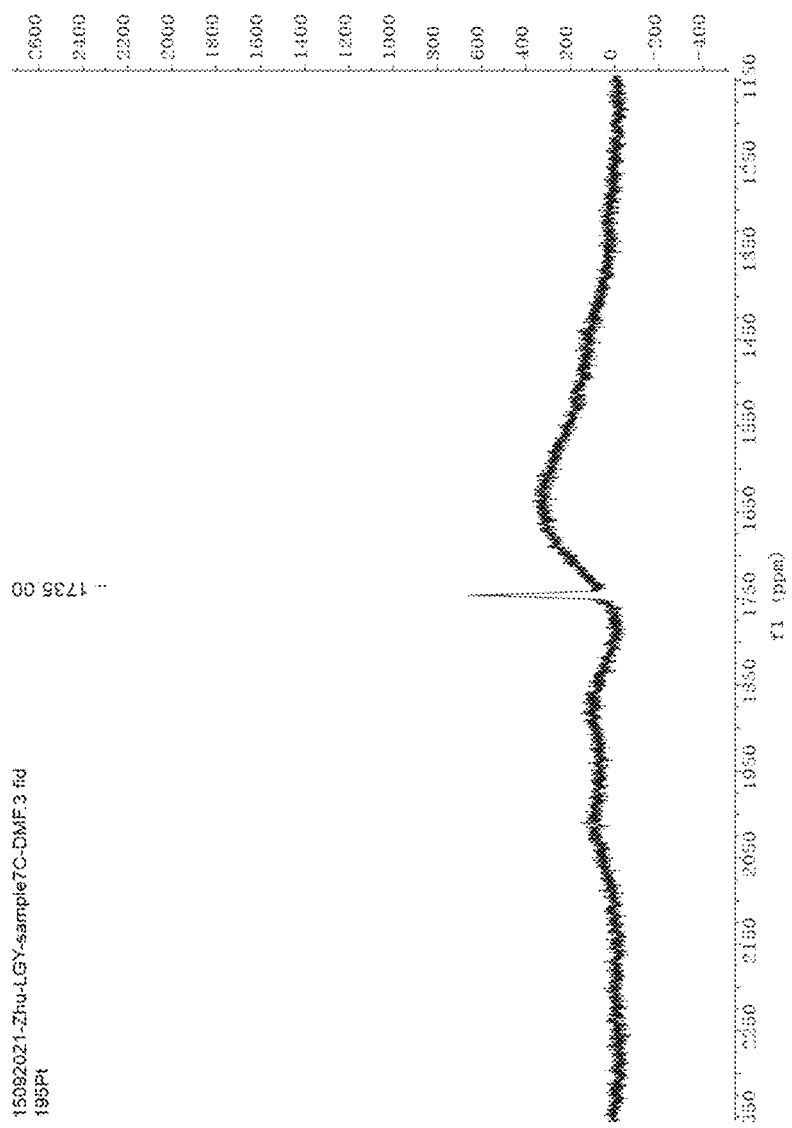
FIG. 3C shows a $^{195}$Pt NMR spectrum of complex 1 prepared in an embodiment of the present invention.
Figure 4A:
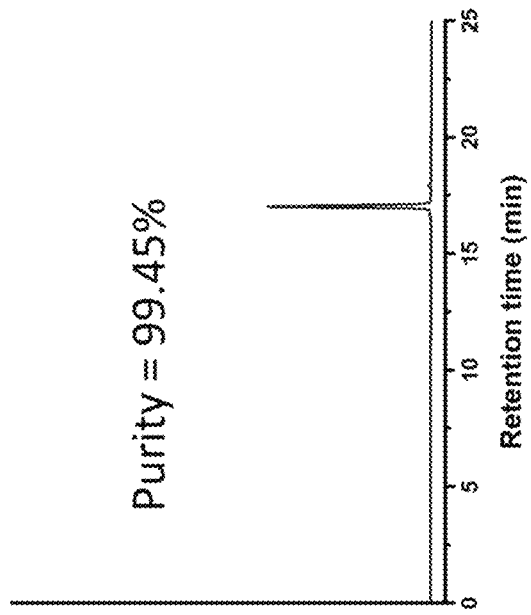
FIG. 4A shows a HR-MS spectrum of complex 1 prepared in an embodiment of the present invention. The insert shows a stimulated MS spectrum of complex 1.
Figure 4B:
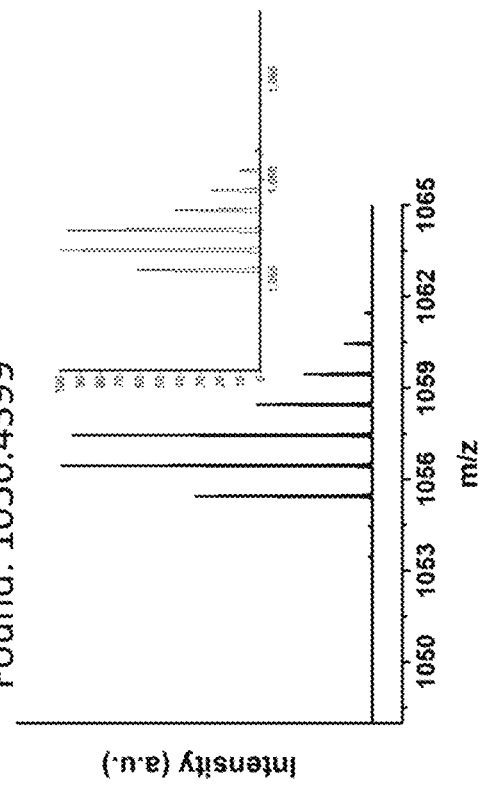
FIG. 4B shows a reverse phase high pressure liquid chromatography (RP-HPLC) chromatogram of complex 1 prepared in an embodiment of the present invention, illustrating the purity of complex 1.

Specifically, NaOH (19.3 mg, 0.270 mmol) was dissolved in 3 mL DMF and 3-(4-hydroxyphenyl)propionic acid (20.0 mg, 0.075 mmol) was added dropwise in ice bath and under $N_2$ protection. Then, commercially available IR780 iodide (40.0 mg, 0.060 mmol, in 5 mL dry DMF) was slowly added over a period of 30 min. The reaction was further kept at 298 K for another 1 h. After washing with $Et_2O$ and silica column chromatography (eluent: DCM/MeOH=8/1), reddish-green crystalline solid was obtained as ligand 1 (22.1 mg, 48.8%). $^1$H NMR (300 MHz, Methanol-$d_4$) δ(ppm) 8.01 (d, J=14.1 Hz, 2H), 7.44-7.34 (m, 4H), 7.32-7.18 (m, 6H), 7.09-7.01 (m, 2H), 6.17 (d, J=14.1 Hz, 2H), 4.09 (t, J=7.2 Hz, 4H), 2.81 (dt, J=34.1, 6.9 Hz, 6H), 2.54 (t, J=6.9 Hz, 2H), 2.11-2.01 (m, 2H), 1.85 (q, J=7.5 Hz, 4H), 1.35 (s, 12H), 1.03 (t, J=7.5 Hz, 6H). HR-MS (m/z): [M]$^+$ calculated for $C_{45}H_{53}N_2O_3^+$: 669.4051, found: 669.3998. (FIGS. 2A and 2B)

c,t-[Pt(1,1-cyclobutane-dicarboxylate)($NH_3$)$_2$($OH$)$_2$] (20.2 mg, 0.05 mmol), ligand 1 (10.0 mg, 0.05 mmol), 1-ethyl-3-(3-dimethylaminopropyl)carbodiimide (EDCI, 0.20 mmol) (TBTU, 19.2 mg, 0.06 mmol), and N-hydroxysuccinimide (NHS, 0.20 mmol) were dissolved in 2 mL DMSO. The reaction was kept for 24 h at 298 K in the dark, then 10 mL of cold water was added to precipitate the yielded product. After silica column chromatography (eluent: DCM/MeOH=6/1) and recrystallization with DCM/$Et_2O$=1/3, dark green powder was obtained as complex 1 (11.2 mg, 37.3%). $^1$H NMR (300 MHz, DMSO-$d_6$) δ(ppm) 7.80 (d, J=14.2 Hz, 1H), 7.50 (d, J=7.5 Hz, 1H), 7.41-7.33 (m, 2H), 7.25-7.16 (m, 2H), 7.03 (d, J=8.7 Hz, 1H), 6.17 (d, J=14.2 Hz, 1H), 4.10 (t, J=7.5 Hz, 3H), 2.68 (d, J=6.9 Hz, 3H), 2.43-2.29 (m, 1H), 2.29 (t, J=6.0 Hz, 1H), 1.93 (d, J=6.3 Hz, 1H), 1.70 (dt, J=14.3, 7.2 Hz, 3H), 0.92 (t, J=7.5 Hz, 4H). $^{13}$C NMR (151 MHz, DMSO-$d_6$) δ(ppm) 180.01, 172.16, 163.35, 158.40, 158.34, 141.37, 136.06, 130.41, 128.93, 125.22, 122.87, 121.87, 111.71, 49.02, 32.26, 31.80, 31.25, 27.68, 21.19, 20.82, 16.19, 15.95, 11.55. $^{195}$Pt NMR (129 MHz, DMF-$d_7$) δ(ppm) 1735.00 (s). HR-MS (m/z): [M]$^+$ calculated: 1056.4445, found: 1056.4399. (FIGS. 3A to 3C and FIG. 4A) The purity of the complex is 99.45% as determined by analytical RP-HPLC. (FIG. 4B)

Example 2

Stability of Complex 1

The stability of complex 1, i.e., complex 1 in phosphate buffer saline (PBS) buffer, cell culture medium such as RPMI-1640, and cell lysate in the dark (i.e., in the absence of radiation) was determined. To determine the stability of complex 1 in PBS, complex 1 (10 µM) was dissolved in PBS buffer (pH 7.4, 1% DMF) and incubated at 310 K in the dark.

At 24 h, the sample was analyzed by HPLC to determine the percentage of Pt(IV) remained. To determine the stability of complex 1 in complete RPMI-1640 culture medium (containing 10% FBS, 2 mM L-Glutamine, and 100 IU mL$^{-1}$ penicillin/streptomycin) or cell lysate (from A2780 cells by 1% triton X-100 lysis, protein concentration adjusted to 1.5 mg mL$^{-1}$), complex 1 was dissolved in these two solutions, respectively (with 1% DMF). At determined time intervals, 50 μL of samples were taken out and diluted with 200 μL MeOH with subsequent centrifugation at 14,000×g to remove proteins, and then the supernatant was analyzed by HPLC.

Figure 5A:
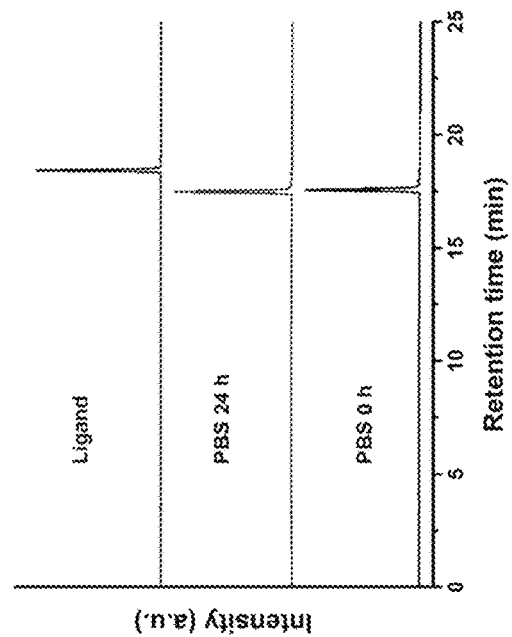
FIG. 5A shows a RP-HPLC chromatogram of complex 1 (10 μM) in phosphate buffer saline (PBS) (pH 7.4) measured by a UV-Vis detector at 700 nm.
Figure 5B:
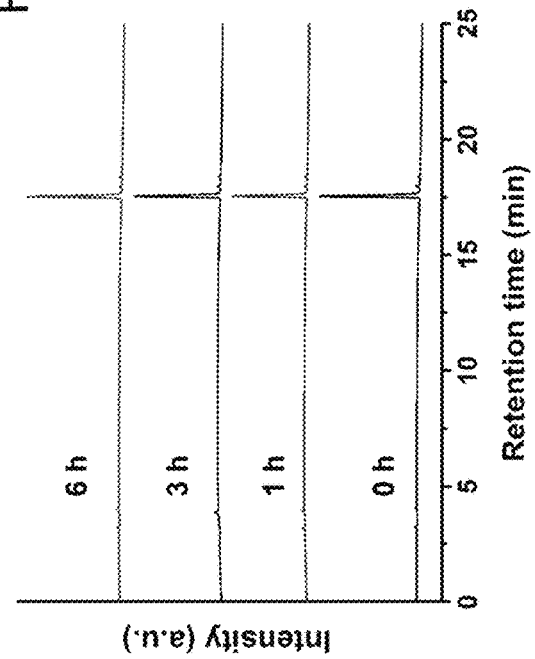
FIG. 5B shows a RP-HPLC chromatogram of complex 1 (10 μM) in RPMI-1640 culture medium measured by a UV-Vis detector at 700 nm.
Figure 5C:
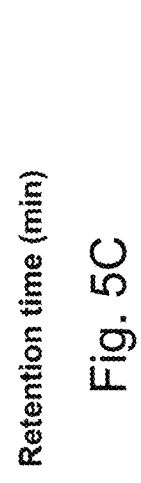
FIG. 5C shows a RP-HPLC chromatogram of complex 1 (10 μM) in cell lysate of A2780 cells measured by a UV-Vis detector at 700 nm.

As shown in FIGS. 5A to 5C, only a single peak representing complex 1 was observed in all three tested environments, indicating that complex 1 is stable in the dark at least for 6 hours.

Example 3

Sono-Activation of Complex 1

Figure 6B:
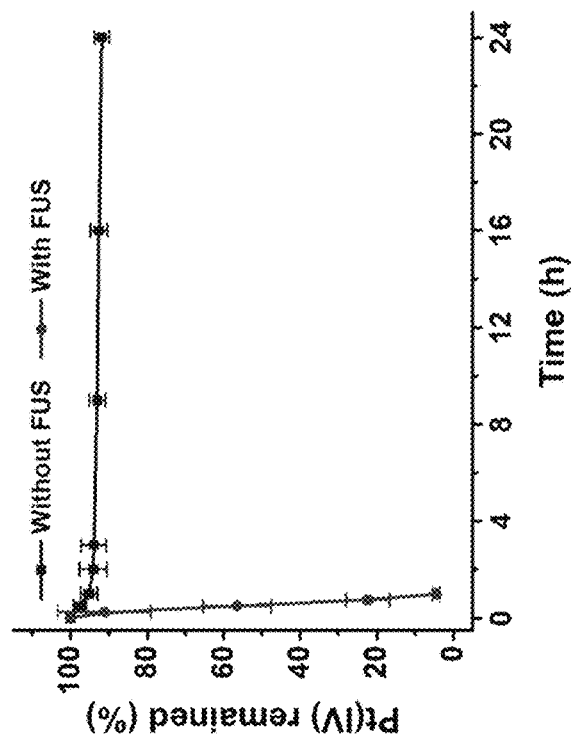
FIG. 6B shows a plot of percentage of Pt(IV) remained against time illustrating the reduction profile of complex 1 in the presence or absence of sono-activation corresponding to FIG. 6A.
Figure 6A:
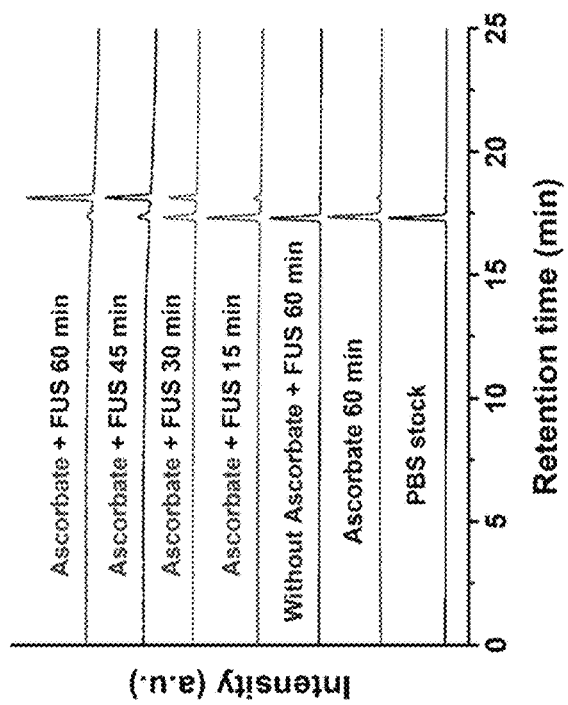
FIG. 6A shows a RP-HPLC chromatogram of a PBS solution containing complex 1 (10 μM) with or without 5 mM ascorbate in the presence or absence of sono-activation (ultrasound: 1.75 MHz, 4 W, 0-60 min) at 37° C.
Figure 6C:
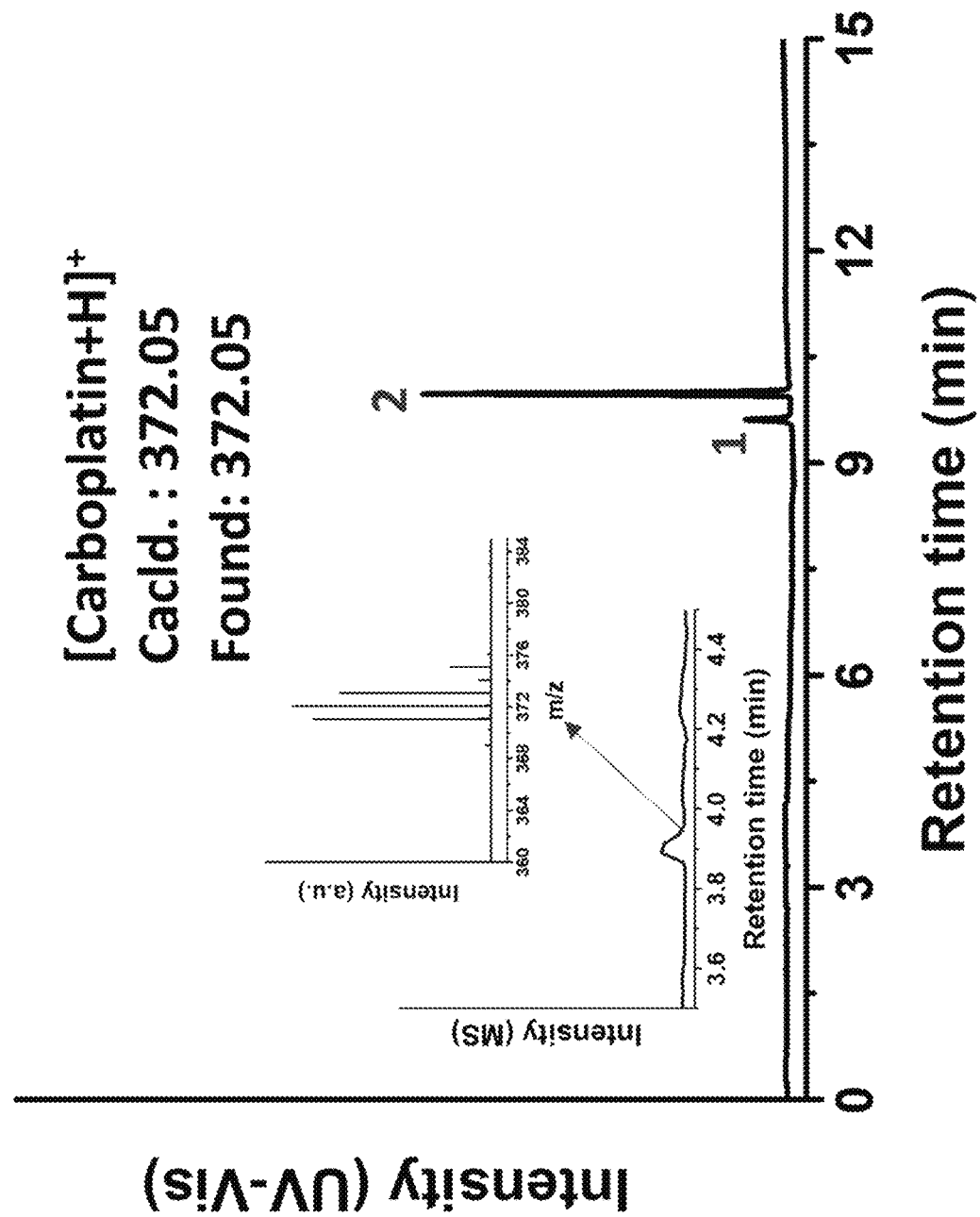
FIG. 6C shows the LC chromatograph of the products of complex 1 after subjecting to sono-activation (4 W, 45 min) in PBS with 5 mM ascorbate. The insert shows the LC chromatogram and MS spectrum of the released carboplatin (i.e. the platinum(II) complex having a structure of Formula (XIII)). The LC chromatograms were measured by a UV-Vis detector at 700 nm.
Figure 6E:
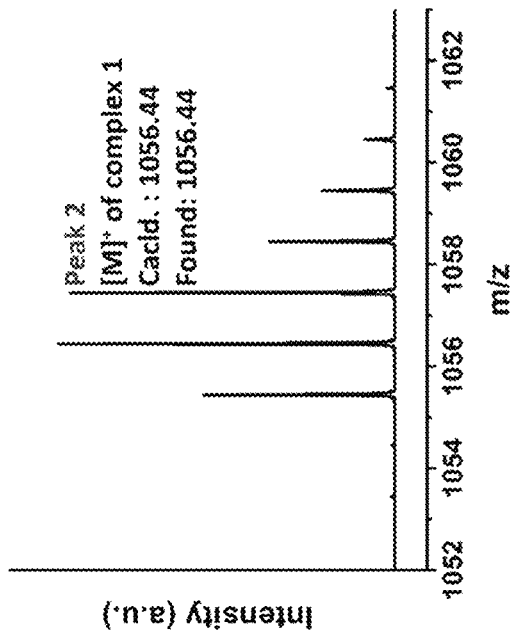
FIG. 6E shows a HR-MS spectrum of complex 1 corresponding to FIG. 6C.
Figure 6D:
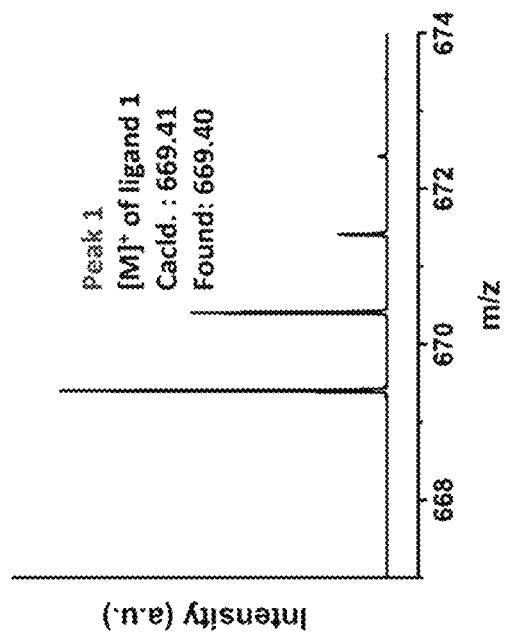
FIG. 6D shows a HR-MS spectrum of ligand 1 corresponding to FIG. 6C.

The sono-activation property of complex 1 was investigated. A PBS solution (with 1% DMF) containing 10 μM complex 1 with or without 5 mM sodium ascorbate (i.e. the sample), was continuously treated with ultrasound (1.75 MHz, 4 W) for a total period of time of 60 min. The sample temperature was monitored with an FLIR thermographic camera and maintained at 37° C. throughout the experiment. As shown in FIG. 6A, under ultrasonication in the presence of ascorbate, the peak of complex 1 in the HPLC chromatogram quickly decreases and with a new peak emerges correspondingly. Further analysis on the HPLC eluent of "FUS 45 min" sample by LC and HR-MS indicates that there three components, including carboplatin, ligand 1 and (unreacted) complex 1. (FIGS. 6C to 6E), indicating the reduction of Pt(IV) to Pt(II) along with the dissociation of the axial ligand 1 and hydroxide ligand upon sono-activation (i.e. complex 1 undergoes a sono-induced reduction). As shown in FIGS. 6A and 6B, about 95% complex 1 was reduced (to Pt(II)) after subjecting to sono-activation for about 60 min. Noteworthy, the sono-induced reduction only occurs under the condition where both ascorbate and ultrasound are present, suggesting the high sensitivity of complex 1 towards the activation environment (FIGS. 6A and 6B).

Figure 7F:
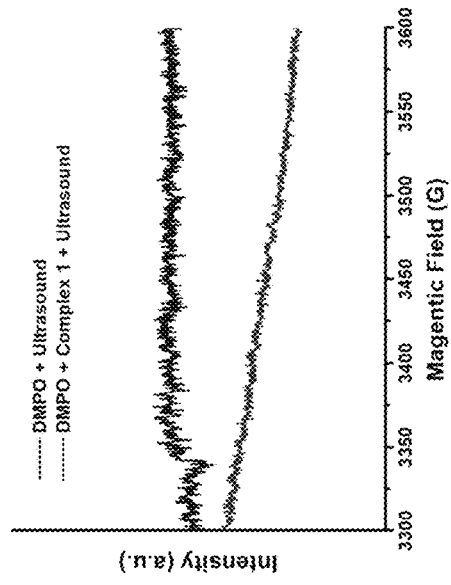
FIG. 7F shows the electroparamagnetic resonance spectra of a mixture of complex 1 and DMPO in the presence of FUS activation (4 W, 15 min).
Figure 7D:
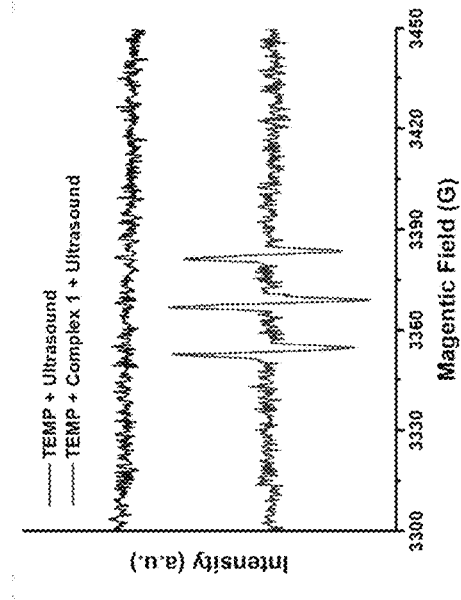
FIG. 7D shows the electroparamagnetic resonance spectra of a mixture of complex 1 and TEMP in the presence of FUS activation (4 W, 15 min).
Figure 7E:
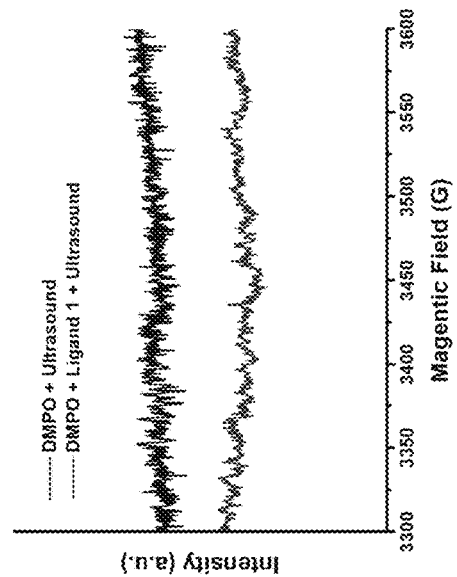
FIG. 7E shows the electroparamagnetic resonance spectra of a mixture of ligand 1 and 5,5-dimethyl-1-pyrroline N-oxide (DMPO) in the presence of FUS activation (4 W, 15 min).

The inventors further investigate the possibility of ROS generation of complex 1 upon sono-activation, by using a hydroxyl radical scavenger, 5,5-dimethyl-1-pyrroline N-oxide (DMPO), and a singlet oxygen scavenger, 2,2,6,6-tetramethyl-piperidine (TEMP), and the singlet oxygen sensor green (SOSG) to investigate the electron transfer process. As shown in FIGS. 7A and 7B, a strong emission profile originating from SOSG was observed for both the ligand 1 and complex 1 activated with FUS, indicating the release of singlet oxygen by ligand 1 and complex 1 upon sono-activation. The release of singlet oxygen by ligand 1 and complex 1 upon sono-activation was further evidenced by their electroparamagnetic resonance spectra with the presence of TEMP. As shown in FIGS. 7C and 7D, signal pulses were observed only when ligand 1 and complex 1 were subjected to ultrasound treatment. In contrast, as shown in FIGS. 7E and 7F, when TEMP was replaced with DMPO, no signal pulse was observed even under ultrasonication. Based on the above, it is suggested that ligand 1 and/or complex 1 releases singlet oxygen (such as by way of a Type II electron transfer process) instead of releasing hydroxyl radicals upon sono-activation.

Example 4

Photo-Activation of Complex 1

Figure 8:
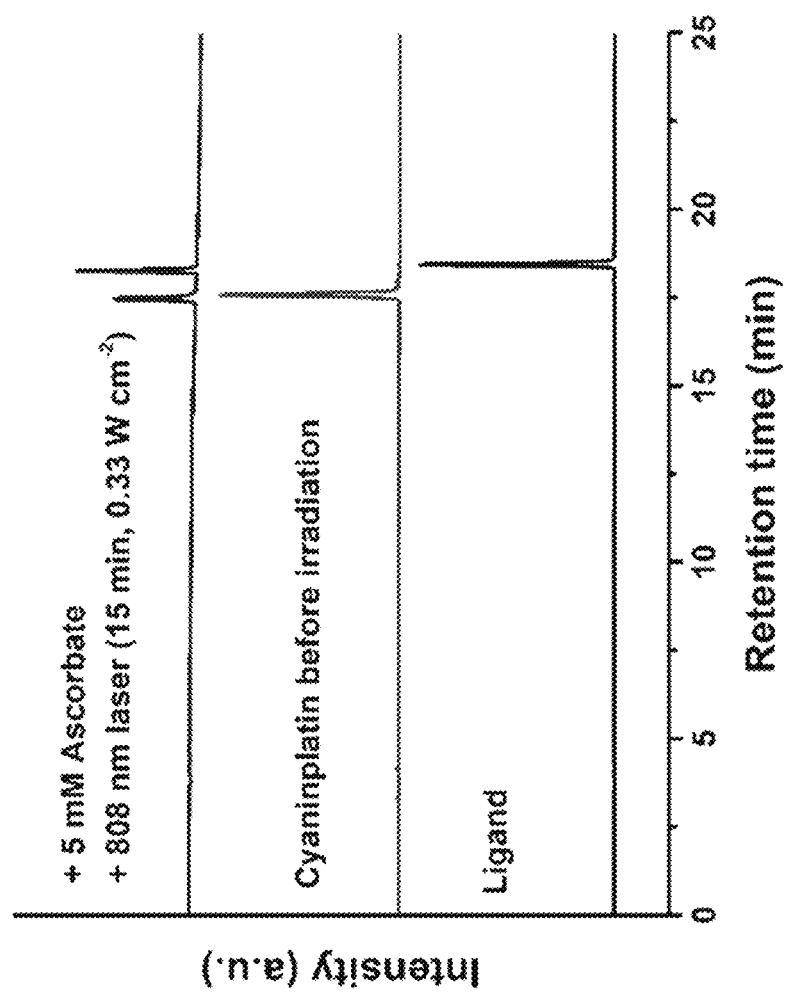
FIG. 8 shows RP-HPLC chromatograms of ligand 1 and complex 1 with or without activated by a 808 nm laser (330 mW/cm$^2$, 15 min).

The inventors have further investigated if complex 1 could be activated by other types of radiation such as EM radiation, in particular light such as infrared light. A PBS buffer solution (with 1% DMF) containing 10 μM complex 1 with 5 mM ascorbate in a quartz cuvette was irradiated with a laser (808 nm, 3.3 mW/cm$^2$) for 15 min under stirring. The sample was analysed by HPLC. As shown in FIG. 8, the peak profile is similar to FIG. 6A where complex 1 was activated by ultrasound. That said, complex 1 can be photo-activated and undergo photo-induced reduction to form and release a Pt(II) complex upon irradiation. In view of the similar profiles, the inventors believe that complex 1 would also release singlet oxygen upon photo-activation along with the aforementioned photo-induced reduction.

Example 5

Cytotoxicity of Complex 1

The biological activity of complex 1 was evaluated. Human breast carcinoma MCF-7 cells, human cervix carcinoma HeLa cells, mammary breast carcinoma 4T1 cells, human lung carcinoma A549 cells, and cisplatin-resistant A549cisR cells were cultured in DMEM containing 10% FBS and 100 IU mL$^{-1}$ penicillin/streptomycin. Human ovarian carcinoma A2780 and A2780cisR cells were cultured in RPMI-1640 containing 10% FBS, 2 mM L-glutamine, and 100 IU mL$^{-1}$ penicillin/streptomycin. Human lung fibroblast MRC-5 cells were cultured in MEM containing 10% FBS, 1% NEAA, 1% L-Glutamine, 1% sodium pyruvate, and 100 IU mL$^{-1}$ penicillin/streptomycin. In every two passages of A2780cisR and A549cisR cells, 5 μM of cisplatin was added to maintain the platinum resistance. All the cells were cultured in humidified incubators at 37° C. with 5% CO$_2$. Cell counting was performed with a hemocytometer.

Cytotoxicity test was performed by exposing the cancer cells with complex 1. The viability of cancer cells exposed was evaluated by means of MTT assay. Specifically, the cells were first pre-seeded in 6-well plates until the confluency reached 80%. Then, the medium was removed and replaced with fresh medium containing different concentrations of complex 1 with 0.5% DMF (0, 2.5, 5, 12.5, 25, or 40 μM). After 30 min, the medium was aspirated, the well was washed with PBS for three times. The cells were trypsinized and resuspended in 2 mL Eppendorf tubes with 1 mL fresh culture medium, followed by treatment with ultrasound (3.5 W, 15 min). After the ultrasound treatment, the cells were seeded into 96-well plates (2×10$^4$ per well), and MTT assay was conducted after 24 h. The experiments were performed in triplicates, and the 100% cell viability was defined as the viability of cells treated with 0.5% DMF (30 min) as vehicle control.

Figure 10:
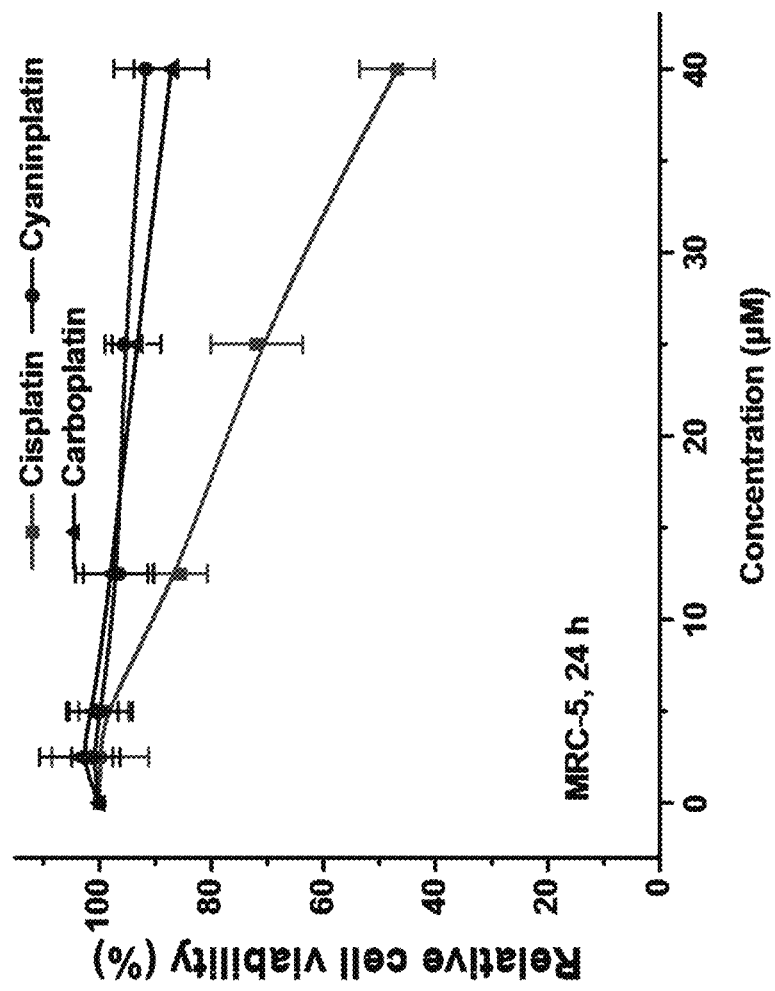
FIG. 10 shows a plot of relative cell viability of MRC-5 cells treated with different concentrations of cisplatin, carboplatin, and cyaninplatin of MRC-5 cells for 24 h.

As shown in FIG. 9, complex 1 is generally non-toxic to the tested cells without the ultrasound treatment, but become very active upon ultrasound treatment. In particular, the sono-sensitization index (SI), which reflects the fold-increase of cytotoxicity (or fold-decrease of IC$_{50}$ value) of the sono-activated complex 1 as compared with the unactivated complex 1, indicates that the cytotoxicity of the activated complex 1 was increased by at least about 6 folds, particularly about 6 folds to about 20 folds as compared with the unactivated complex 1. In addition, without wishing to be limited by theory, the inventors have found that the fold-increase of cytotoxicity (in terms of SI value) was generally much higher than those with the use of a mixture of carboplatin and ligand 1 (1:1 eq.) under the same ultrasound treatment conditions. That said, complex 1 in fact exhibited significantly stronger inhibitory effect on the tested cells as compared with the mixture. Noteworthy, this effect is even more pronounced when the tested cells are cisplatin-resistance cancer cells, with a SI of >9.8 (A2780-cisR) and >9.3 (A549-cisR) for the activated complex 1 as compared with a SI of >1.7 (A2780-cisR) and >2.1 (A549-cisR) for the activated mixture. Furthermore, complex 1 is non-toxic to the tested normal human lung fibroblasts MRC-5 cells in the absence of ultrasound, indicating its biosafety to normal cells (FIG. 10).

Figure 11A:
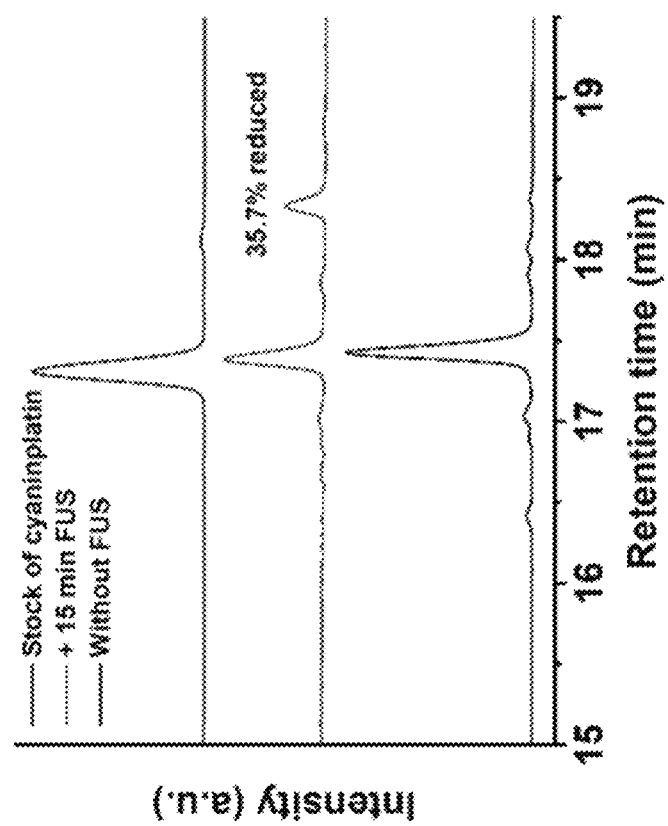
FIG. 11A shows a HPLC chromatogram of complex 1 (12.5 μM) extracted from A549 cells by lysis at 6 h after activation with or without focused ultrasound (FUS) (3.5 W, 15 min).
Figure 11B:
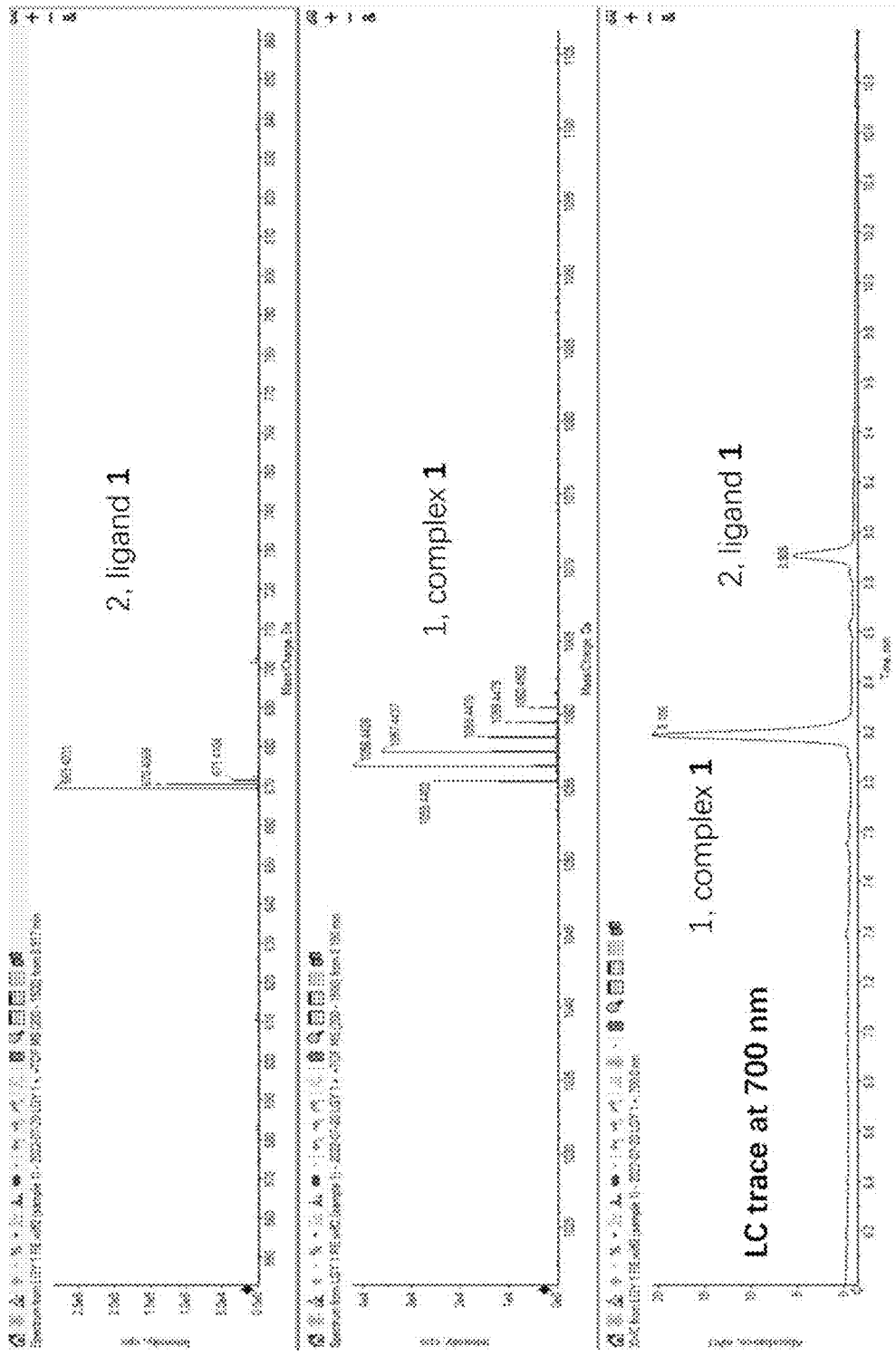
FIG. 11B shows a LC-MS spectra of the extract from the cell lysate of FIG. 11A without FUS activation.
Figure 11C:
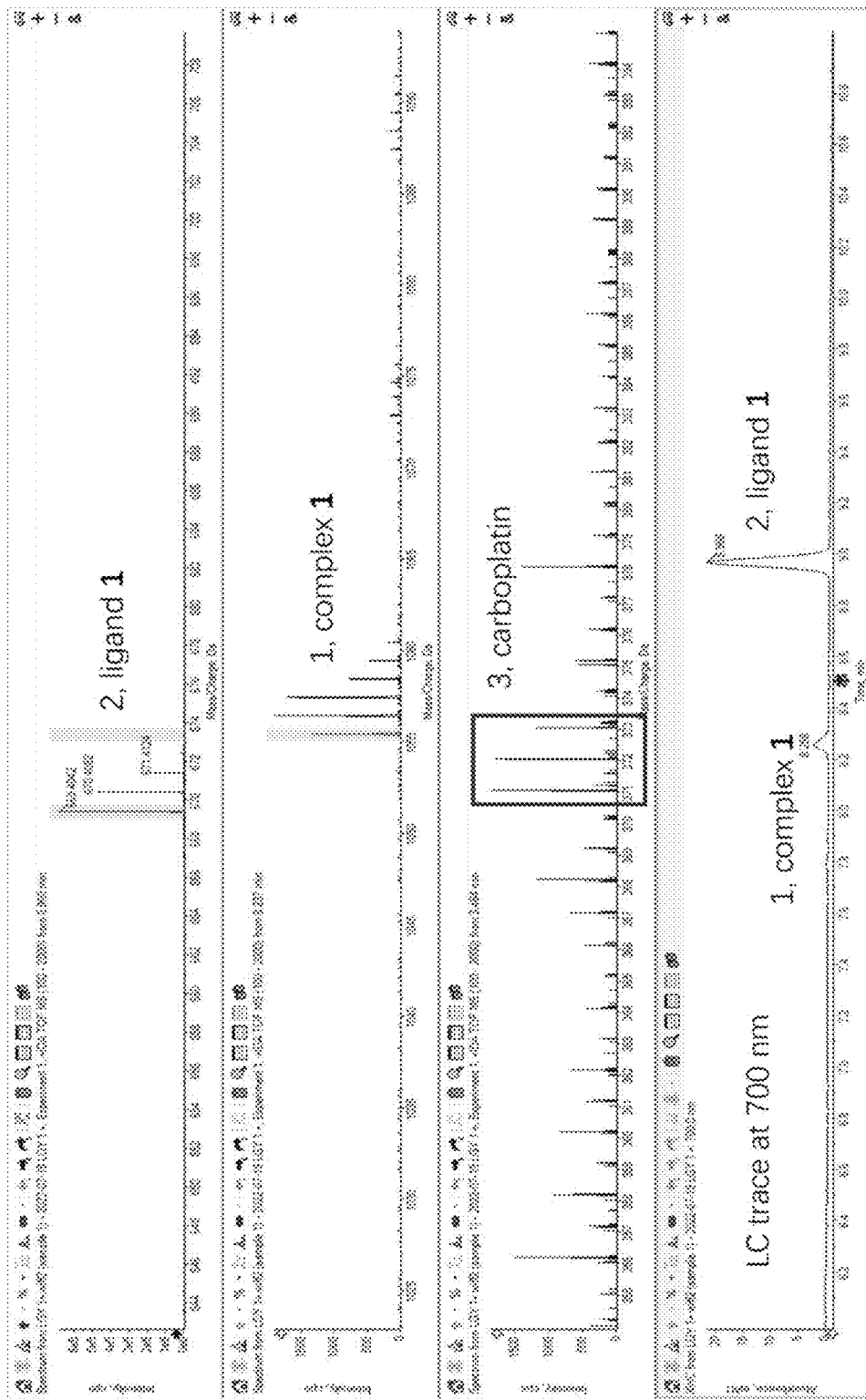
FIG. 11C shows a LC-MS spectra of the extract from the cell lysate of FIG. 11A with FUS activation.

To further confirm that whether complex 1 is reduced to carboplatin in cells, complex 1 was extracted via lysis of A549 cells which were treated with 12.5 μM complex 1 and activated by 3.5 W FUS for 15 min, and analysed by HPLC. As shown in FIG. 11A, a new peak was only observed with the complex treated with ultrasound. It is believed that such peak represents 35.7% of complex 1 that has been converted into its reduced form, i.e. carboplatin upon ultrasound activation. The inventors thus further analyzed the extract/eluent of FIG. 11A via LC-MS, and confirmed that the new peak in FIG. 11A corresponds to carboplatin.

Based on the above, it is thus believed that with a short period of time of ultrasound activation, such as for 15 min, is already sufficient to allow the complex to be reduced to its reduced form. In addition, such a short period time requirement may minimize the side effect such as the local development of hyperthermia upon ultrasound activation. Furthermore, it is also believed that the complex of the present invention is suitable to be used as a prodrug against cancer, particularly cisplatin-resistant cancer as it is found that the complex is stable without ultrasound treatment even in the presence of cellular reductant such as ascorbate at physiological concentrations.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A platinum complex comprising a structure of Formula (I):

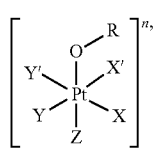

Formula (I)

wherein:

X, X', Y, Y' and Z are independently selected from the group consisting of ammonia, hydroxide, halide, oxalate, diamines, dicarboxylate, glycolate and —OR, optionally X and X' are linked to form a first bidentate ligand, and/or Y and Y' are linked to form a second bidentate ligand;

n is selected from the group consisting of zero, any positive charge, and any negative charge;

R is a radiation-responsive moiety having a structure of Formula (II):

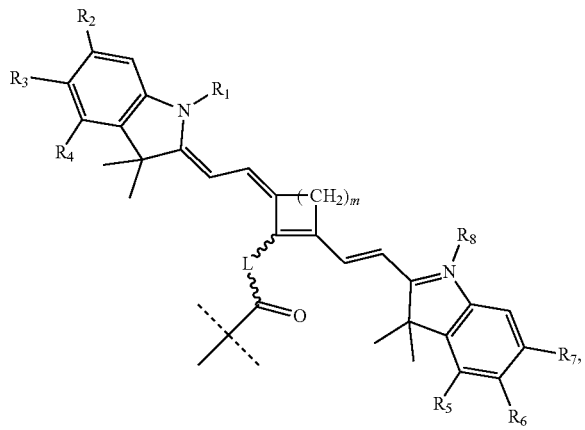

Formula (II)

with L being a linker group being selected from the group consisting of:

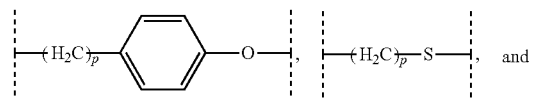, and

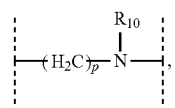, wherein p is selected from the group consisting of of 1, 2, 3 and 4, and $R_{10}$ is selected from the group consisting of H, a linear C1-C6 alkyl group, a branched C1-C6 alky group, and a functional side chain;

m is 0, 2 or 3;

$R_1$ and $R_8$ are independently selected from the group consisting of a linear or branched alkyl chain, a sulfonate-containing group, a carboxyl group, a carboxylate ester-containing group, and a heterocyclic group; and $R_2$ to $R_7$ are each independently selected from the group consisting of a hydrogen, a halogen, and an adjacent pair of $R_2$ to $R_7$ forming a fused 6-membered carbocyclic ring.

2. The platinum complex as claimed in claim 1, wherein Z is not —OR.

3. The platinum complex as claimed in claim 1, having a structure of Formula (III):

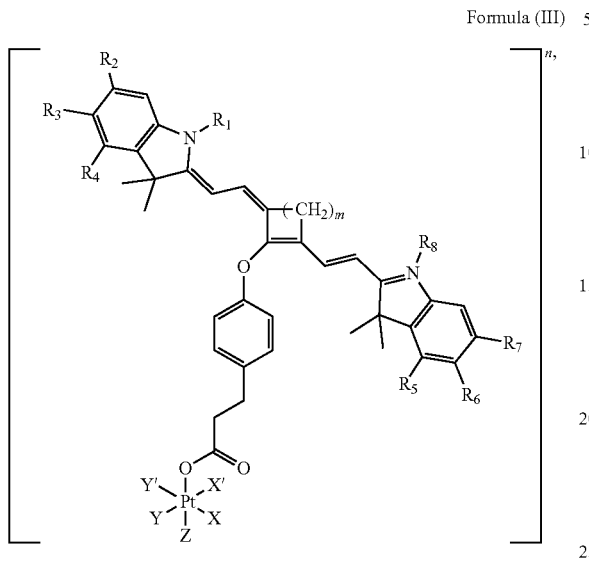

Formula (III)

wherein:

either X and X' or Y and Y' are linked to a bidentate ligand; and

Z is hydroxide or —OR.

4. The platinum complex as claimed in claim 3, wherein X and X' are linked to form a dicarboxylate; Y and Y' are ammonia; and Z is hydroxide.

5. The platinum complex as claimed in claim 3, wherein $R_1$ and $R_8$ are independently selected from the group consisting of —$CH_3$, —$(CH_2)_2CH_3$, —$(CH_2)_2COOH$, —$(CH_2)_5COOH$, —$(CH_2)_4SO_3H$,

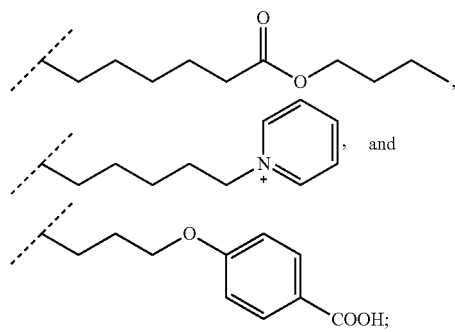

and wherein $R_2$ to $R_7$ are either each independently selected from the group consisting of a hydrogen, chloride, iodide, and bromide, or an adjacent pair of $R_2$ to $R_7$ are fused to form a benzene ring.

6. The platinum complex as claimed in claim 3, having a structure of Formula (IIIa)

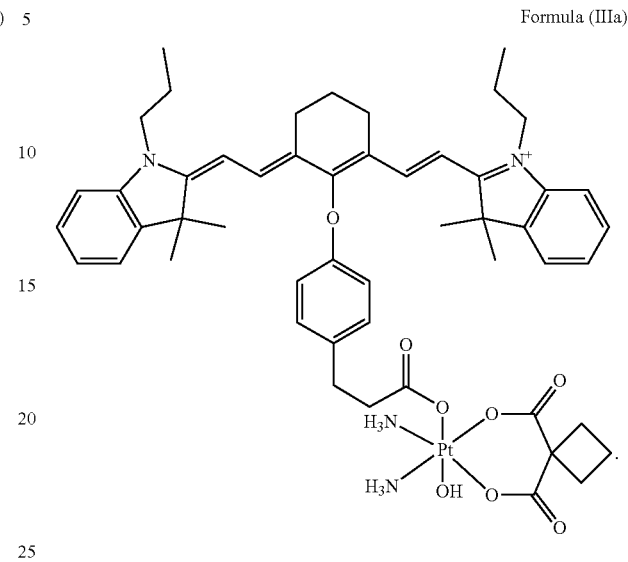

Formula (IIIa)

7. The platinum complex as claimed in claim 1, wherein the complex is reducible to a reduced form and generates reactive oxygen species by exposure to radiation.

8. A pharmaceutical composition comprising a platinum complex as claimed in claim 1 and including a pharmaceutically acceptable carrier.

9. A method of treating a target tissue, comprising administering to a patient in need thereof a platinum complex as claimed in claim 1 and administering to the target tissue radiation in an amount and of a frequency effective to activate the complex.

10. The method as claimed in claim 9, wherein the radiation is ultrasound.

11. The method as claimed in claim 10, wherein the ultrasound has a frequency between about 1 MHz to about 3 MHz.

12. The method as claimed in claim 11, wherein the ultrasound is applied at a power of about 1 W to about 4 W.

13. The method as claimed in claim 9, wherein the radiation is light.

14. The method as claimed in claim 13, wherein the light has a frequency of between about 350 THz to about 500 THz.

15. The method as claimed in claim 14, wherein the light is applied at a power intensity from about 3 mW/cm$^2$ to about 350 mW/cm$^2$.

16. The method as claimed in claim 9, wherein the target tissue is a tumor.

17. The method as claimed in claim 16, wherein the tumor is selected from the group consisting of cervical cancer, lung cancer, ovarian cancer, breast cancer and mammary cancer.

18. The method as claimed in claim 16, wherein the tumor has an intrinsic or acquired cisplatin-resistance.

19. The method as claimed in claim 9, wherein the platinum complex acts as a prodrug.

* * * * *